US010641767B2

(12) United States Patent
Campbell et al.

(10) Patent No.: US 10,641,767 B2
(45) Date of Patent: *May 5, 2020

(54) MULTIPLE HYBRID IMMUNOASSAY

(71) Applicant: Abbott Point of Care Inc., Princeton, NJ (US)

(72) Inventors: John Lewis Emerson Campbell, Woodlawn (CA); Pamela Anne Frank, Nepean (CA); Meghan Elizabeth Hawkes, Ottawa (CA); Shannon Reishma Lobin, Woodlawn (CA); Cary James Miller, Ottawa (CA); Zhen Yang, Kanata (CA)

(73) Assignee: Abbott Point of Care Inc., Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/975,145

(22) Filed: May 9, 2018

(65) Prior Publication Data
US 2018/0259511 A1    Sep. 13, 2018

Related U.S. Application Data

(60) Division of application No. 14/994,713, filed on Jan. 13, 2016, now Pat. No. 9,995,744, which is a
(Continued)

(51) Int. Cl.
*G01N 33/543* (2006.01)
*G01N 33/68* (2006.01)
(Continued)

(52) U.S. Cl.
CPC ........ *G01N 33/54386* (2013.01); *B01L 3/502* (2013.01); *B01L 3/50273* (2013.01);
(Continued)

(58) Field of Classification Search
CPC ........ G01N 33/54386; G01N 33/6893; G01N 33/545; G01N 33/54353; G01N 33/54313;
(Continued)

(56) References Cited

U.S. PATENT DOCUMENTS 3,720,760 A    3/1973    Bennich et al.
3,857,931 A    12/1974   Hager
(Continued)

FOREIGN PATENT DOCUMENTS

EP    0 310 132 A    4/1989
WO    WO 97/19955 A    6/1997
(Continued)

OTHER PUBLICATIONS

European Office Action dated May 11, 2012 in corresponding European Application No. 03 771 940.8-2404.
(Continued)

*Primary Examiner* — Melanie Brown
(74) *Attorney, Agent, or Firm* — Kilpatrick Townsend & Stockton LLP

(57) ABSTRACT

The invention relates to compositions and methods for the immunoassay of an analyte of interest. The analyte is detected in an immunoassay using three or more antibodies, where in each antibody specifically binds to a different epitope on the analyte. When the analyte of interest in a clinical marker for an acute disease, the detection of the analyte by immunoassay is a diagnosis of the occurrence of the disease.

4 Claims, 14 Drawing Sheets

Related U.S. Application Data continuation of application No. 14/081,309, filed on Nov. 15, 2013, now Pat. No. 9,267,939, which is a continuation of application No. 10/208,560, filed on Jul. 29, 2002, now abandoned.

(51) Int. Cl.
  B01L 3/00       (2006.01)
  G01N 33/53      (2006.01)
  G01N 33/545     (2006.01)

(52) U.S. Cl.
  CPC ......... *G01N 33/53* (2013.01); *G01N 33/5302* (2013.01); *G01N 33/543* (2013.01); *G01N 33/545* (2013.01); *G01N 33/54313* (2013.01); *G01N 33/54353* (2013.01); *G01N 33/6887* (2013.01); *G01N 33/6893* (2013.01); *B01L 2400/0683* (2013.01); *G01N 2333/47* (2013.01); *G01N 2333/4712* (2013.01); *G01N 2800/324* (2013.01)

(58) Field of Classification Search
  CPC ............... G01N 33/5302; G01N 33/53; G01N 33/6887; G01N 33/543; B01L 3/50273; B01L 3/502
  See application file for complete search history.

(56) References Cited

U.S. PATENT DOCUMENTS

| | | | |
|---|---|---|---|
| 4,210,418 A | | 7/1980 | Brown et al. |
| 4,353,982 A | | 10/1982 | Gomez et al. |
| 4,433,059 A | | 2/1984 | Chang et al. |
| 4,514,505 A | | 4/1985 | Canfield et al. |
| 4,595,661 A | | 6/1986 | Cragle et al. |
| 4,624,930 A | | 11/1986 | Tanswell et al. |
| 4,737,456 A | | 4/1988 | Weng et al. |
| 4,804,626 A | | 2/1989 | Bellet et al. |
| 4,808,521 A | | 2/1989 | Allen |
| 4,880,731 A | | 11/1989 | Kaspar |
| 4,885,255 A | | 12/1989 | Stock et al. |
| 5,011,771 A | | 4/1991 | Bellet et al. |
| 5,096,669 A | | 3/1992 | Lauks et al. |
| 5,187,067 A | | 2/1993 | Koike et al. |
| 5,202,234 A | | 4/1993 | Shah et al. |
| 5,324,650 A | | 6/1994 | Obzansky et al. |
| 5,416,026 A | | 5/1995 | Davis et al. |
| 5,447,440 A | | 9/1995 | Davis et al. |
| 5,514,253 A | | 5/1996 | Davis et al. |
| 5,554,339 A | | 9/1996 | Cozzette et al. |
| 5,593,638 A | | 1/1997 | Davis |
| 5,599,677 A | * | 2/1997 | Dowell ............ G01N 33/57434 435/7.23 |
| 5,605,664 A | | 2/1997 | Lauks et al. |
| 5,609,824 A | | 3/1997 | Lauks et al. |
| 5,614,416 A | | 3/1997 | Lauks et al. |
| 5,628,961 A | | 5/1997 | Davis et al. |
| 5,789,253 A | | 8/1998 | Lauks et al. |
| 5,795,725 A | * | 8/1998 | Buechler ............ G01N 33/6887 435/7.1 |
| 5,821,061 A | | 10/1998 | Hattori et al. |
| 5,821,095 A | | 10/1998 | Hattori et al. |
| 6,030,827 A | | 2/2000 | Davis et al. |
| 6,114,180 A | | 9/2000 | Doth et al. |
| 6,140,474 A | | 10/2000 | Kamada et al. |
| 6,180,340 B1 | | 1/2001 | Nelson et al. |
| 6,379,883 B2 | | 4/2002 | Davis et al. |
| 687,851 A1 | | 4/2005 | Landegren |
| 6,942,771 B1 | | 9/2005 | Kayyem |
| 7,419,821 B2 | | 9/2008 | Davis et al. |
| 7,638,292 B2 | | 12/2009 | Eriksson et al. |
| 2004/0018577 A1 | | 1/2004 | Campbell et al. |
| 2010/0167301 A1 | | 7/2010 | Collier et al. |
| 2010/0311185 A1 | | 12/2010 | Schelp et al. |
| 2014/0141484 A1 | | 5/2014 | Campbell et al. |
| 2016/0123976 A1 | | 5/2016 | Campbell et al. |

FOREIGN PATENT DOCUMENTS

| | | |
|---|---|---|
| WO | WO 01/36666 A1 | 5/2001 |
| WO | WO 01/59425 A1 | 8/2001 |

OTHER PUBLICATIONS

Se-Kyung Oh et al., "Use of a Dual Monoclonal Solid Phase and a Polyclonal Detector to Create an Immunoassay for the Detection of Human Cardiac Troponin I", Clinical Biochemistry, vol. 33, No. 4, Jun. 1, 2000, pp. 255-262, XP 001182264.
I. Chibata, Immobilized Enzymes, Halsted Press, New York, 1978, pp. 1-284.
Cuatrecasas, "Protein Purification by Affinity Chromatography, Derivatizations of Agarose and Polyacrylamide Beads", The Journal of Biological Chemistry, vol. 245, No. 12, Issue of Jun. 25, pp. 3059-3065, 1970 (7 Pages).
Bangs TechNote #201, "Working with Microspheres", © 2002, Bangs Laboratories, Inc. (20 Pages).
Bangs TechNote #204, "Adsorption to Microspheres", © 1999, Bangs Laboratories, Inc. (6 Pages).
Bangs TechNote #205, "Covalent Coupling", © 2002, Bangs Laboratories, Inc. (11 Pages).
Seradyn Technical Method Bulletin, "Recommended Adsorption and Covalent Coupling Procedure", 1999.
Wong, Chemistry of Protein Conjugation and Cross-Linking, 1991, CRC Press, Boca Raton, Fl.
Pierce Instructions, ImmunoPure IgG1 Fab and F(ab')2 Preparation Kit, #44880, © Pierce Biotechnology, Inc., Jan. 2007 (3 Pages).
Pierce Instructions, SMCC, Sulfo-SMCC, #22360, #22322, © 2011 Thermo Fisher Scientific Inc. (4 Pages).
Pierce Instructions, EZ-Link Maleimide Activated Phosphatase Kit, #31493, © Pierce Biotechnology, Inc., Jan. 2006 (5 Pages).
D. Beale, 1987, Molecular Framentation: Some Applications in immunology, Exp Comp Immunology 11, 287-296.
E. Lamoyi, 1986, Preparation of F(ab')2 fragments from mouse IgG of various subclasses, Meth Enz 121, 652-663.
King, TP, Kochoumian, L., 1979, A comparison of different enzyme-antibody conjugates for enzyme-linked immunosorbent assay, J Immun Meth 28, 201-210.
Brinklay, MA (1992), A survey of methods for preparing protein conjugates with dyes, haptens and crosslinking reagents, Bioconj Chem 3, 2-13.
European Office Action for EP Application No. 03 771 940.8 dated Jul. 9, 2007 (6 Pages).
European Office Action for EP Application No. 03 771 940.8 dated Oct. 7, 2009 (3 Pages).
European Office Action for EP Application No. 03 771 940.8 dated Mar. 3, 2011 (4 Pages).
Morjana, N.A., "Degradation of Human Cardiac Troponin I After Myocardial Infarction," Biotechnology and Applied Biochemistry, Academy Press, US, vol. 28, No. 2, Oct. 1998, pp. 105-111, XP 001080545, ISSN: 0885-4513.
Filatov, V. L., et al., "Epitope Mapping of Anti-Troponin I Monoclonal Antibodies," Biochemistry and Molecular Biology International, Academic Press, London, GB, vol. 45, No. 6, Sep. 1998,pp. 1179-1187, XP 000941112, ISSN: 1039-9712.
Eriksson, S. et al., "Negative Interference in Cardiac Troponin I Immunoassay from a Frequently Occurring Serum and Plasma Component" Clinical Chemistry, 2003, vol. 49:7, pp. 1095-1104.
Tobias, R. B., "Quantitative ELISA for measuring serum Troponin I," Abstract for poster presented at symposium, C-70, American Association for Clinical Chemistry (2002).
Alpert, et al., "Myocardial Infarction Redefined—A consensus Document of the Joint European Society of Cardiology/American College of Cardiology Committee for the Redefinition of Myocardial Infarction," Journal of American College Cardiology, Sep. 2000, vol. 36, No. 3, pp. 959-969.

(56) References Cited

OTHER PUBLICATIONS

Apple, et al., "Myocardial Infarction Redefined: Role of Cardiac Troponin Testing," Clinical Chemistry 47, 2001, No. 3, pp. 377-379.
Ferrieres, et al., "Human Cardiac Troponin I: Precise Identification of Antigenic Epitopes and Prediction of Secondary Structure," Clinical Chemistry, vol. 44:3, 1998, pp. 487-493.
Harlow, et al., Antibodies, a laboratory manual, Cold Spring Harbor Laboratory, NY, 1998.
Hermanson, G., Bioconjugation techniques, Academic Press, NY 1996.
Dominguez, et al., "Detection of *Streptococcus pneumonia* antigen by a rapid immunochromatographic assay in urine samples," Chest., Jan. 2001, vol. 119(1), pp. 243-249.
Katrukha, et al., "Degradation of cardiac Troponin I: implication for reliable immunodetection," Clin. Chem., Dec. 1998, vol. 44 (12), pp. 2433-2440.
Katrukha, et al., "Troponin I is released in bloodstream of patients with acute myocardial infarction not in free form but as complex," Clin. Chem., Aug. 1997, vol. 43, 8 Pt1, pp. 1379-1385.
Morjana, N., "Degradation of human cardiac troponin I after myocardial infarction," Biotechnol. Appl. Biochem., Oct. 1998, vol. 28, Pt. 2, pp. 105-111.
Ngo, T., (Ed) Electrochemical sensors in immunological analysis, Plenum Press NY, 1987.
Wild, D., (Ed) The immunoassay handbook, Stockton Press NY, 1994.
"Non-Final Office Action" issued in U.S. Appl. No. 14/081,309, dated Jul. 28, 2015, 9 pages.
"Notice of Allowance" issued in U.S. Appl. No. 14/081,309, dated Nov. 6, 2015, 7 pages.
"Non-Final Office Action" issued in U.S. Appl. No. 14/994,713, dated Nov. 24, 2017, 12 pages.
"Notice of Allowance", issued in U.S. Appl. No. 14/994,713 dated Mar. 27, 2018, 11 pages.

\* cited by examiner

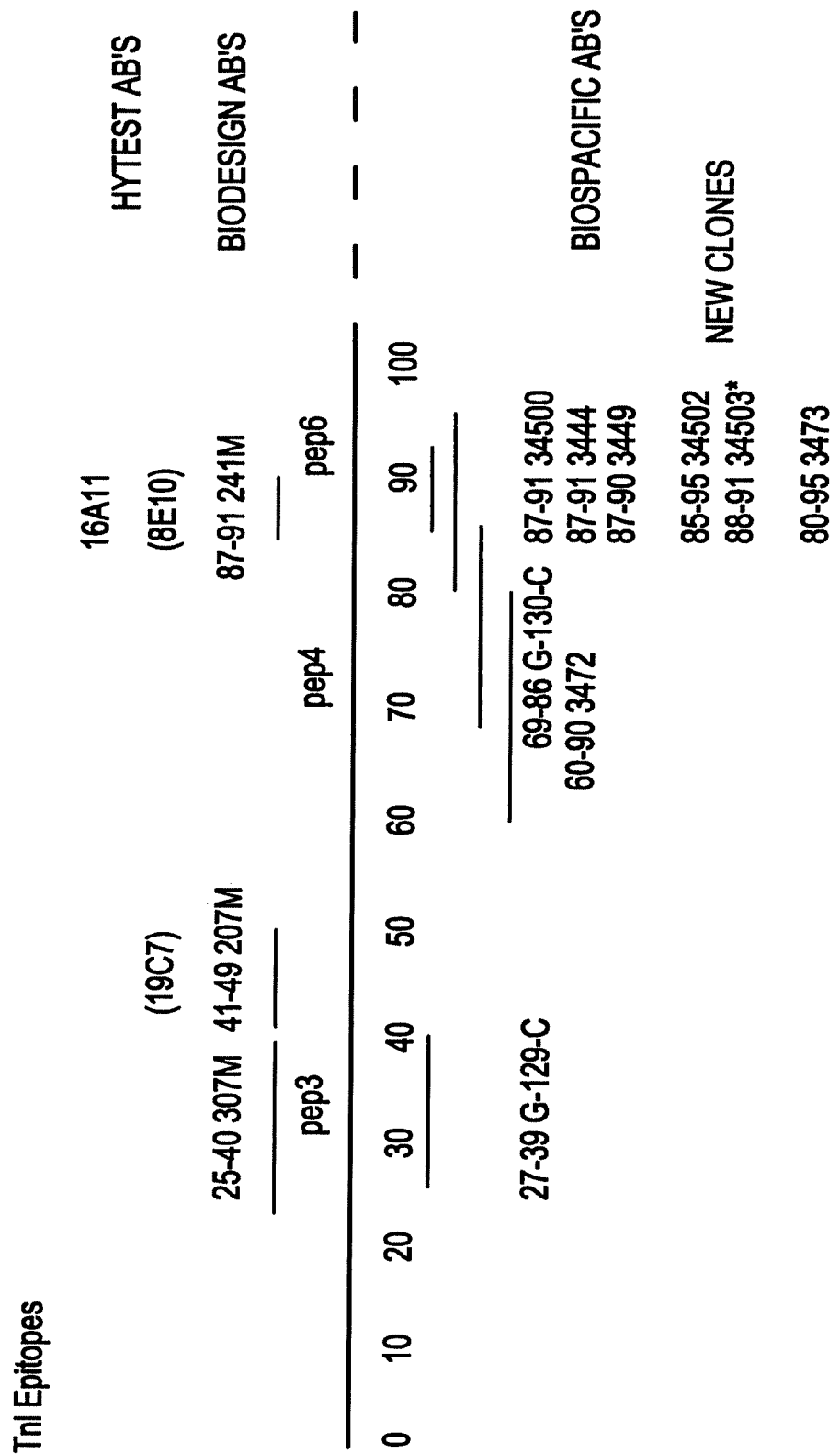

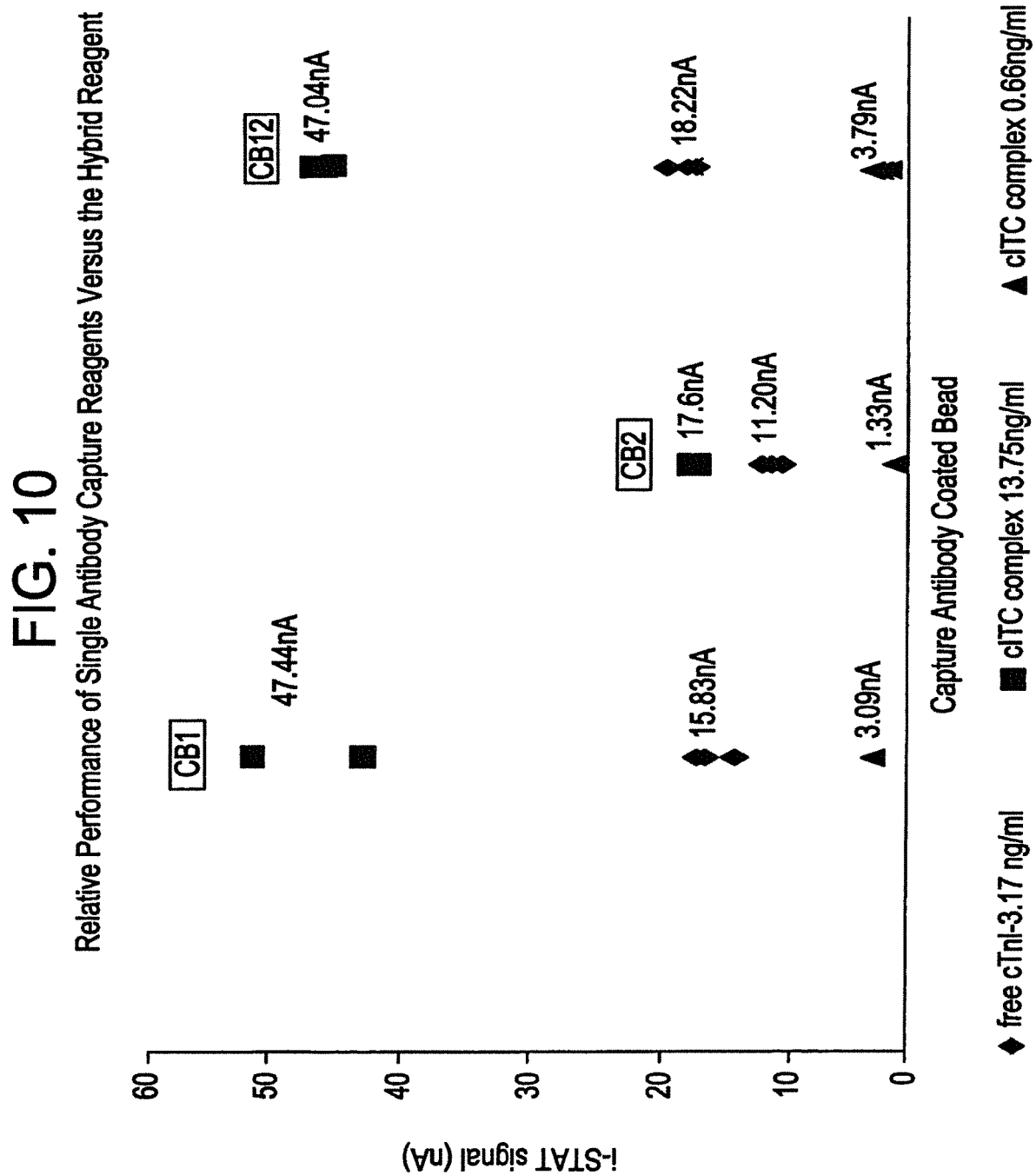

cTnI Signal Stability
ITC complex in whole blood

MULTIPLE HYBRID IMMUNOASSAY

CROSS REFERENCE TO RELATED APPLICATION

This is a divisional of U.S. patent application Ser. No. 14/994,713, filed Jan. 13, 2016, which is a continuation of U.S. patent application Ser. No. 14/081,309, filed Nov. 15, 2013, which is a continuation of U.S. patent application Ser. No. 10/208,560, filed Jul. 29, 2002, the entire contents of which are hereby incorporated by reference.

FIELD OF THE INVENTION

The present invention relates to the diagnosis of diseases and medical events, notably myocardial infarction ("MI"). More specifically, the present invention relates to the detection of a clinical marker of a disease or medical event, in particular MI, using multiple antibodies, each antibody having a different specificity for the clinical marker. The present invention also relates to reagents and apparatuses used in the diagnosis of a disease or medical event, in particular MI.

BACKGROUND

Diagnosis of acute disease is often based on immunoassay, e.g. enzyme-linked immunosorbent assay ("ELISA"), detection of abnormal levels of clinical markers, such as proteins, enzymes and hormones in biological fluids, particularly when the concentration changes quickly during the acute phase of disease. ELISA systems allowing for the rapid and simple diagnosis of the occurrence of an acute disease, such as the occurrence of an MI, are therefore extremely important.

In the past, clinical markers for diagnosing the occurrence of an MI included lactate dehydrogenase ("LDH") and glutamic oxaloacetic transaminase ("GOT"), though these were not very specific. Problems with LDH and GDH led to the use of the MB isoenzyme of creatine kinase ("CK-MB") as a clinical marker for the diagnosis of MI. However, CK-MB can also be found in skeletal muscle and in blood after skeletal muscle injury. Thus, CK-MB is not completely specific for cardiac muscle. Another disadvantage of CK-MB as a clinical marker of MI is that the level of CK-MB in the skeletal muscle varies with the degree of skeletal muscle regeneration, information which may often not be known when administering a test or analyzing a test result for MI. Another disadvantage of testing for CK-MB is that CK-MB levels remain elevated for only 2-3 days after the onset of chest pain. For patients admitted after that time, the CK-MB test will be of limited value. Thus, due to the lack of specificity when assaying CK-MB, and the limited time frame for its use as a diagnostic tool, CK-MB is not an ideal clinical marker for diagnosing MI.

Cardiac troponin 1 ("cTnI") is now used as an accurate cardiac-specific biological parameter detectable in serum very soon after MI and remaining present for more than 2-3 days after the onset of MI. Troponin is present in cardiac tissue as a complex of three subunits: Troponin T ("TnT"), the tropomyosin binding subunit, Troponin C ("TnC"), the $Ca^{2+}$ binding subunit; and Troponin I ("TnI"), the sub-unit which inhibits the actomyosin $Mg^{2+}$ ATPase. TnI is a thin filament regulatory protein complex, which confers calcium sensitivity to the cardiac and striated muscle.

Human Troponin I exists in three isoforms: two skeletal muscle isoforms (fast and slow) (MW=19.8 kDa) and a cardiac TnI isoform ("cTnI") with an additional 31 residues on the N-terminus resulting in a molecular weight of 23 kDa (209 amino acids). Cardiac TnI is uniquely located in the myocardium where it is the only isoform present. Cardiac TnI rapidly appears in human serum (within approximately 4 to 6 hours) following a MI. It reaches a peak level after 18-24 hours and remains at elevated levels in the blood stream for up to 6-10 days. As a result, cTnI released into the circulation from the myocardium is very specific for myocardial injury.

Elevated cTnI levels in blood may be used to diagnose MI and distinguish other heart related events and diseases. Immunoassay systems capable of accurately detecting human cTnI would be valuable to the medical community for diagnosing the occurrence of MI. For more information on the utility of cTnI testing, see Apple and Wu, Myocardial infarction redefined: Role of cardiac troponin testing. Clinical Chemistry 47, 377-9, (2001), which is hereby incorporated by reference.

Cardiac TnI exists in multiple subforms in blood as a result of modifications such as proteolytic cleavage, phosphorylation, chemical oxidation, chemical reduction, cleavage of amino acid residues, and chemical modification of amino acid moieties. For example, amino acids 1 to 25 and 150 to 209 are generally not found on cTnI subforms in serum as a result of proteolysis. The many different subforms of cTnI circulating in the bloodstream are predominantly found in complexes with other proteins. See Katrukha (1997). For example, cTnI may be complexed with cTnT and cTnC ("cITC").

In many instances, the chemical modifications and complexation of cTnI in the bloodstream eliminate or block the binding sites for ELISA reagents on some subforms of cTnI, thereby making the epitopes of the ELISA reagents unavailable for binding. For more information on cTnI epitopes and cTnI instability, see Morjana et al., Degradation of Human cardiac troponin I after myocardial infarction: Biotechnol. Appl. Biochem. (1998), 28, 105-111; Gaelle Ferrieres et al. Human cardiac troponin 1: precise identification of antigenic epitopes and prediction of secondary structure: Clin. Chem. (1998), 44, 487-493; Katrukha et al., Troponin I is released in bloodstream of patients with acute myocardial infarction not in free form but as complex: Clin. Chem. (1997), 43, 1379-1385; and Katrukha et al., Degradation of cardiac troponin I: implication for reliable immunodetection: Clin. Chem. (1998), 44, 2433-244, which are incorporated herein by reference.

For most commercially important clinical marker analytes, a number of efficient monoclonal antibodies have been developed which bind a particular epitope of an analyte. The difference between antibodies are the specific location of binding to the analyte, affinity for the analyte, and cross-reactivity with other potential interferents within the sample. ELISA assays have been traditionally developed by pairwise testing of available antibodies for use either as the capture reagent or signal reagent.

In the development of ELISA assays for cTnI, much effort has been expended in optimizing the antibody and enzyme reagents used. However, the likelihood of epitopes being unavailable for binding on the many subforms of cTnI present in serum and complexation with other proteins makes detection of cTnI significantly difficult and typically cause current ELISA reagents to underestimate actual cTnI levels in a sample. Furthermore, the many different subforms of cTnI with different epitopes available for binding cause current ELISA assays to give significantly different results from sample to sample, from reagent set to reagent set, and as a function of time.

Thus, there exists a need to develop methods of detecting a clinical marker and subforms thereof, in particular cTnI, for the diagnosis of an acute disease event, in particular MI. The present invention satisfies this need and provides reagents, kits, and apparatuses for detecting a clinical marker and subforms thereof, in particular cTnI.

SUMMARY

The present invention is related to the detection of an analyte of interest. The analyte of interest may be cTnI. In an exemplary embodiment of the present invention, an immunoassay composition for detecting an analyte of interest may comprise three or more antibodies, wherein each antibody is capable of binding to a different epitope on the analyte. At least two of the three different antibodies which bind to the analyte are also capable of binding to at least two different epitopes on a subform of the analyte. At least one of the epitopes on the analyte of interest is unavailable for binding on the subform.

In another exemplary embodiment of the present invention, an immunoassay device for detecting an analyte of interest may comprise two or more antibodies, wherein each antibody binds to a different epitope on the analyte and wherein the two or more antibodies are bound to at least one surface. At least one of the two different antibodies which bind to the analyte is also capable of binding to at least one different epitope on a subform of the analyte. At least one of the epitopes on the analyte of interest is unavailable for binding on the subform.

In another exemplary embodiment of the present invention, an immunoassay kit for detecting an analyte of interest may comprise three or more antibodies, wherein each antibody is capable of binding to a different epitope on the analyte. At least two of the three different antibodies which bind to the analyte are also capable of binding to at least two different epitopes on a subform of the analyte. At least one of the epitopes on the analyte of interest is unavailable for binding on the subform.

In another exemplary embodiment of the present invention, a sandwich immunoassay product may comprise an analyte of interest and a subform of the analyte. At least three different epitopes on the analyte are available for binding by at least three different antibodies. At least three different antibodies are bound to different epitopes on the analyte. At least two of the three epitopes on the analyte are available for binding on the subform. At least two of the at least three antibodies are bound to different epitopes on the subform. At least one of the epitopes on the analyte of interest is unavailable for binding on the subform.

In another exemplary embodiment of the present invention, a patient may be diagnosed for the occurrence of an acute disease, such as myocardial infarction, by applying a sample obtained from the patient to a surface comprising at least two antibodies which bind to different epitopes on cTnI, wherein at least one of the two antibodies is capable of binding to a different epitope on a subform of cTnI, and wherein at least one epitope of the at least two antibodies is unavailable for binding on the subform. A third antibody is then added which binds to yet another epitope on cTnI and the subform. The extent of binding of the third antibody to cTnI and the subform is then measured.

BRIEF DESCRIPTION OF THE DRAWINGS

FIG. 9 depicts the primary structure of subform of cardiac troponin I (cTnI) without amino acids 1 to 25 and 150 to 209, and shows the location for epitopes of the cTnI antibodies. In FIG. 9, abbreviated names are utilized for at least some antibodies. The abbreviated names 3472, 34500, 3444, 3449, 34502, and 3473 (in FIG. 9) are equivalent to antibodies A34720, A34500, A34440, A34490, A34502, and A34730, respectively.

FIG. 10 shows the amperometric signals from different single-use assays prepared with a first capture antibody (CBI), a second capture antibody (CB2), or a combination of first and second capture antibodies (CB12) to a whole blood sample spiked with free cTnI and two levels of cITC complex.

DETAILED DESCRIPTION

1. Definitions

Figure 1:
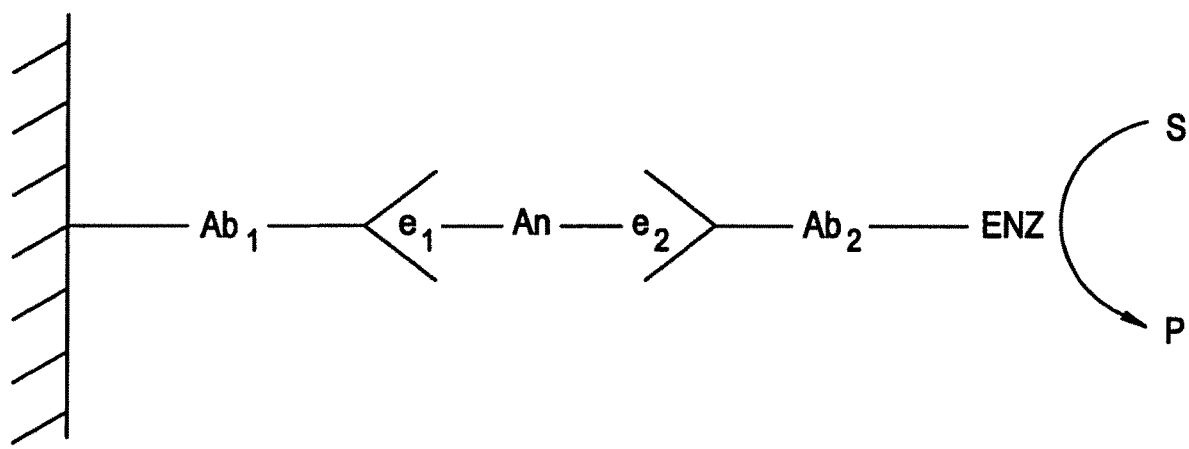
FIG. 1 shows the standard sandwich assay for detecting an analyte of interest, wherein a capture antibody ($Ab_1$) and signal antibody ($Ab_2$) are directed to a first and second epitope ($e_1$ and $e_2$), respectively, of an analyte of interest (An). The signal antibody is labeled with an enzyme (Enz), which is used for signal generation by converting substrate (S) to product (P).

To aid in the understanding of the present invention, several terms are defined below.

"Analyte" means a biological or chemical substance that is capable of being bound by at least three different antibodies, and includes subforms thereof that may be bound by at least three different antibodies.

"Antibody" means a polypeptide or derivative thereof that specifically binds to an epitope on an analyte of interest or subform thereof.

"Capture antibody" or "capture reagent" means an antibody that specifically binds to an analyte of interest or subform thereof, wherein said antibody is immobilized on a surface either (i) before, (ii) after or (iii) during binding to said analyte or subform thereof.

"Detect", "detected," or "detectable," when used to describe a signal of a signal-generating element, means a signal capable of being distinguished from background.

"Epitope" means a binding site for an antibody or other binding member on an analyte of interest or subform thereof. An epitope is "unavailable for binding" if the epitope is either not present or inaccessible for binding by an antibody.

"Immunoassay" or "sandwich immunoassay" means a method of simultaneous sandwich, forward sandwich and reverse sandwich immunoassays, and includes competitive immunoassays thereof, all of which are well understood by those skilled in the art.

"Subform," when used to describe an analyte, means the product of a chemical reaction, a member of a complex with other biological or chemical substances, alternative conformations, or combinations thereof that may be bound by at least two different antibodies.

"Sensing element" means any device or apparatus that is capable of detecting a signal.

"Signal antibody" or "signal reagent" means an antibody that specifically binds to an analyte of interest or subform thereof, wherein said antibody is attached to a signal-generating element via a covalent linkage, hydrophobic interactions, hydrophilic interaction, ionic interactions, Van der Waal forces, or a combination thereof.

"Signal-generating element" means a biological, chemical, or radioactive substance that (i) produces a detectable signal, directly or indirectly, or (ii) is itself detectable.

"Surface" means a support that may be separated from a solution.

2. Analyte

The present invention relates to the detection of an analyte and subforms thereof. The analyte may be a clinical marker of a disease state from a patient believed to have suffered an acute disease event, wherein the clinical marker is also present in one or more subforms. In an acute disease state which is amenable to analysis by this invention, the clinical marker may be a transiently elevated substance in the blood which is released in a significant quantity at, after, or before the time of the acute disease event of interest. The elevated concentration of the clinical marker analyte decreases as endogenous conversion factors act upon the clinical marker to produce subforms of the analyte. Subforms derived from the clinical marker may be transiently elevated in a serial manner, as each is first created then metabolized by endogenous conversion factors. The period of transient elevation may be for as short as a few hours to as long as several weeks.

The analyte may be a biological substance such as a protein, glycoprotein, enzyme, etc., which is released in small quantities at the occasion of an acute disease event such as a heart attack, stroke, or at the occasion of a traumatic injury such as a broken bone or a hematoma. The analyte may be normally absent in such increased quantities and may be converted to a one or more subforms over time by endogenous conversion factors including, but not limited to proteolytic cleavage, phosphorylation, chemical oxidation, chemical reduction, cleavage of amino acid residues, and chemical modification of amino acid moieties. The analyte may be a protein including, but not limited to, TnI, TnT, CK-M, CK-B, myoglobin, hCG, TSH, FSH, pneumococcal PCA, apolipoproteins, C-reactive protein (CRP), brain natriuretic protein (BNP) and its pro-form pro-BNP, human leukocyte antigen and human apolipoproteins. A preferred analyte is cTnI.

Figure 2:
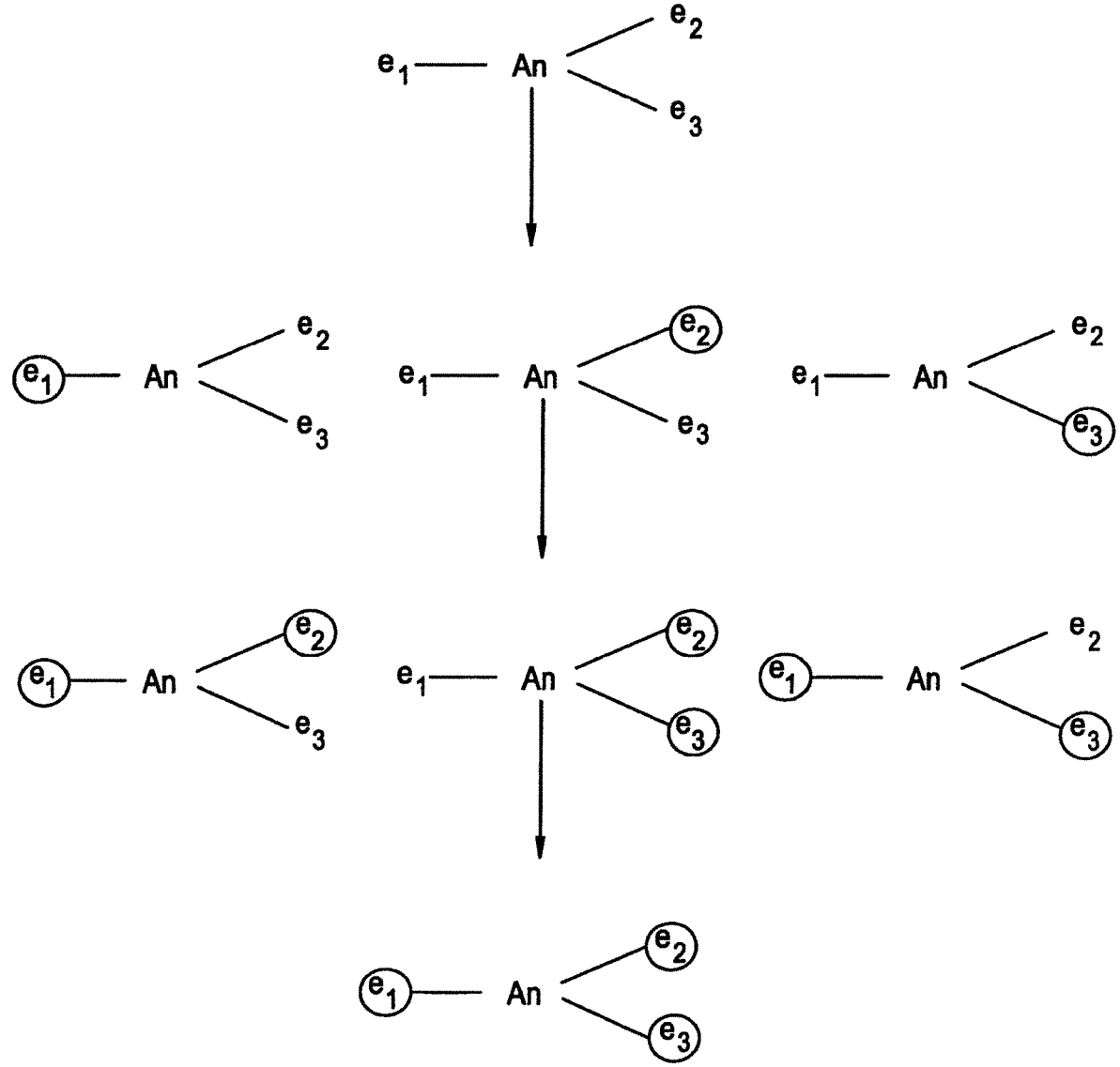
FIG. 2 is a representation of an analyte of interest (An) with three epitopes ($e_1$, $e_2$ and $e_3$). As the analyte is modified, forms complexes or adopts alternative conformations, a subform is produced with one or more of the epitopes unavailable for binding by antibodies. Each epitope that is unavailable for biding is identified by a circle, whereas each epitope that is available for binding is identified without a circle. Each subform may be further modified so that additional epitopes are unavailable for binding by antibodies.

The analyte has at least three different epitopes that are available for binding by an antibody (FIG. 2). A subform of the analyte has at least two different epitopes that are available for binding by an antibody and the epitopes of the subform are also present on the analyte (FIG. 2). At least one epitope of the analyte is unavailable for binding on the subform. An epitope of the analyte unavailable for binding on the subform may be as a result of complexation or alternative conformations, as well as the endogenous conversion factors described above.

The analyte may be in a native or natural form. The analyte may also be a derivative of the native or natural form. For example, in the case of cTnI the analyte may be full length cTnI monomer or a derivative thereof that is either free or part of cITC complex. In addition, the analyte may be any form of cTnI that is released into serum in connection with an MI. The analyte may also be any modified form of cTnI present in serum including, but not limited to, cTnI as shown in FIG. 9. The analyte may also be any modified form of cTnI that has one or more epitopes that are unavailable for binding on any precursor of the analyte. In order to be an analyte, the only requirement is that the modified or derivative form of cTnI must have at least three epitopes available for binding by three different antibodies.

The present invention may also be used to detect an analyte and subforms thereof that are present at low concentration where high sensitivity is required.

3. Immunoassay

Analytes have traditionally been detected using a system based on the sandwich assay depicted in FIG. 1 wherein a first monoclonal or polyclonal antibody for capture is attached to a surface, and a second monoclonal or polyclonal antibody is labeled with a signal-generating element (e.g., an enzyme). For more information on commercial immunoassay products and the technology on which they are based, see Wild, (Ed), The Immunoassay Handbook, Stockton Press NY, 1994, which is incorporated herein by reference. The traditional sandwich assay fails, however, to adequately detect analytes that undergo complexation, alternative conformations or modification that make epitopes for the capture antibody, signal antibody, or both unavailable for binding.

The present invention relates to the use of a sandwich immunoassay for detecting an analyte and one or more subforms thereof (FIG. 2). Subforms of the analyte may be due to causes including mutations, complexation, chemical modification, proteolysis or rearrangement. The present invention may also be used to detect more than one related analyte, such as an active protein and its inactive precursor or a class of similar analytes for which a single detection assay is developed.

Figure 3A:
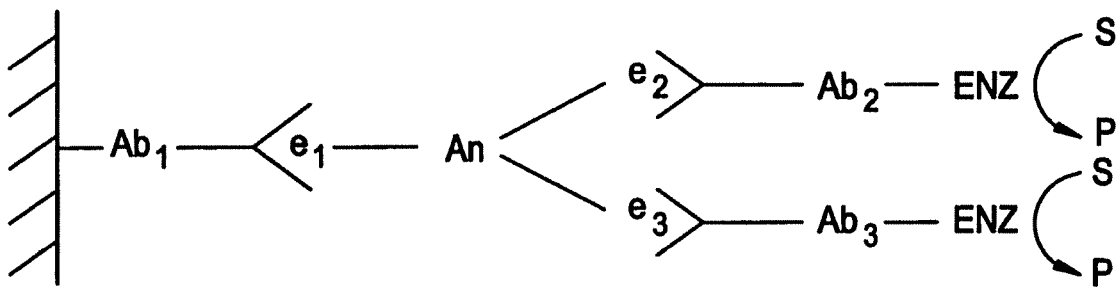
FIG. 3 comprises FIGS. 3A-3C, which show various views of a modified sandwich assay for detecting an analyte of interest (An) and subforms thereof using one capture antibody ($Ab_1$) and more than one signal antibody ($Ab_2$, $Ab_3$). The assay is able to detect the presence of the analyte and all subforms thereof that have at least one epitope for the capture antibody ($e_1$) and at least one epitope for a signal antibody ($e_2$ or $e_3$). All epitopes for binding are shown bound by an antibody; however, the analyte or subforms thereof need to be bound by only one capture antibody and one signal antibody to be detected.
Figure 3B:
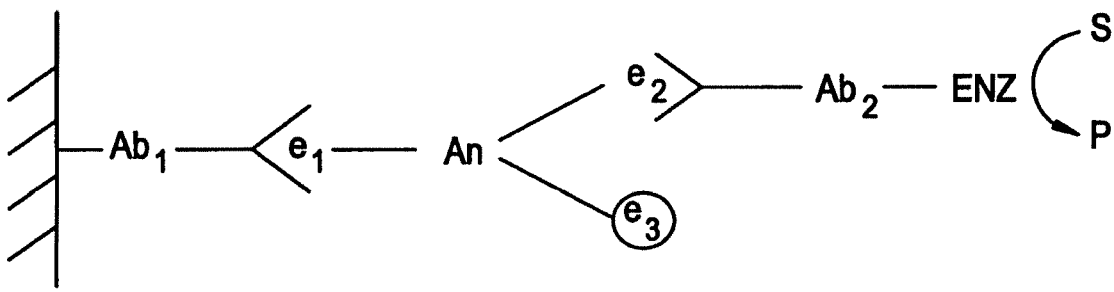
Figure 3C:
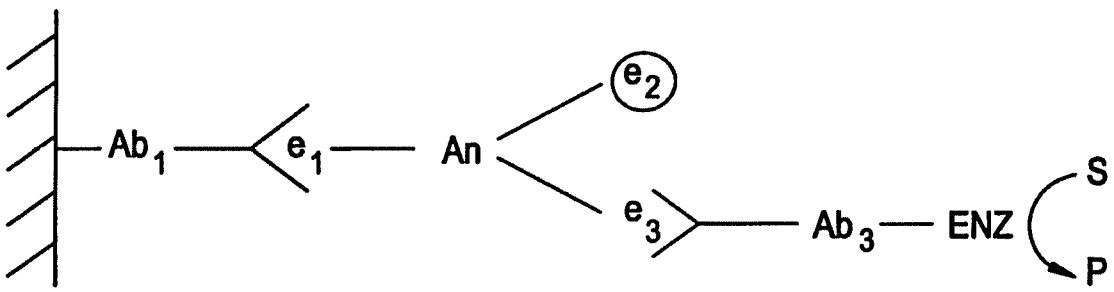
Figure 4A:
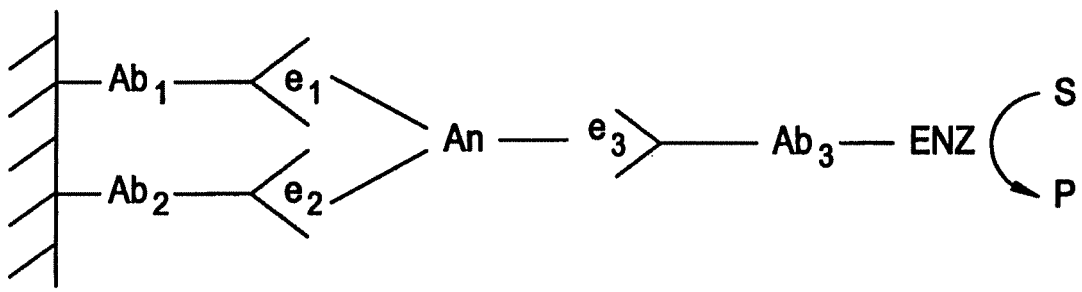
FIG. 4 comprises FIGS. 4A-4C, which show various views of a modified sandwich assay for detecting an analyte of interest (An) and subforms thereof using more than one capture antibody ($Ab_1$ and $Ab_2$) and one signal antibody ($Ab_3$). The assay is able to detect the presence of the analyte and all subforms thereof that have at least one epitope for the signal antibody ($e_3$) and at least one epitope for a capture antibody ($e_1$ or $e_2$). All epitopes for binding are shown bound by an antibody; however, the analyte or subforms thereof need to be bound by only one capture antibody and one signal antibody to be detected.
Figure 4B:
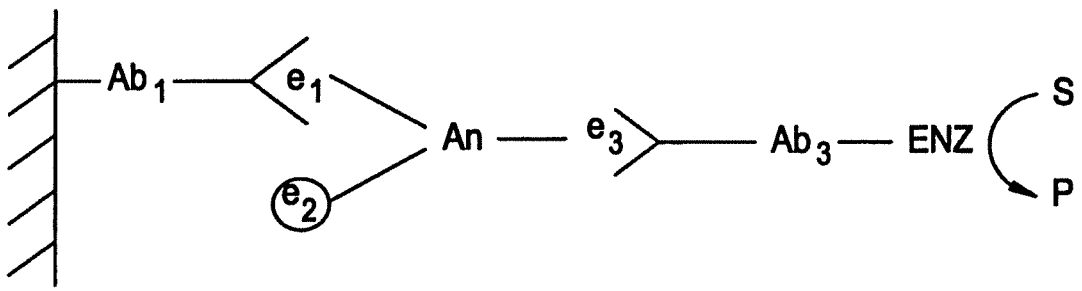
Figure 4C:
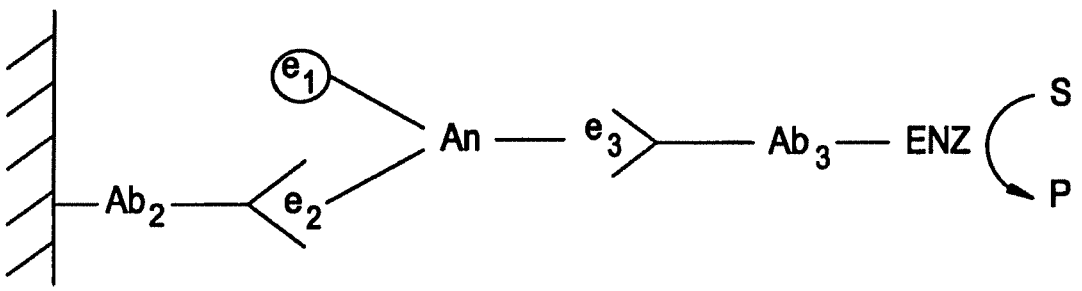
Figure 5A:
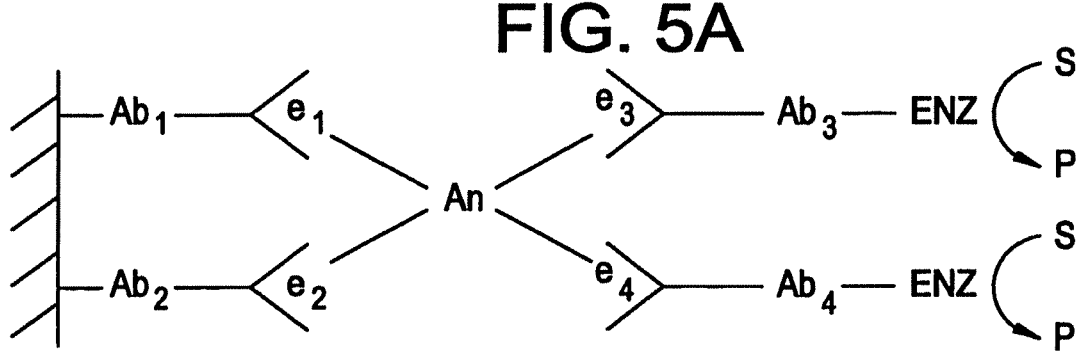
FIG. 5 comprises FIGS. 5A-5I, which show various views of a modified sandwich assay for detecting an analyte of interest (An) suing more than one capture antibody ($Ab_1$ and $Ab_2$) and more than one signal antibody ($Ab_3$ and $Ab_4$). The assay is able to detect the presence of the analyte and all subforms thereof that have at least one epitope for a capture antibody ($e_1$ or $e_2$) and at least one epitope for a signal antibody ($e_3$ or $e_4$). All eptitopes for binding are shown bound by an antibody; however, the analyte or subforms thereof need to be bound by only one capture antibody and one signal antibody to be detected.
Figure 5B:
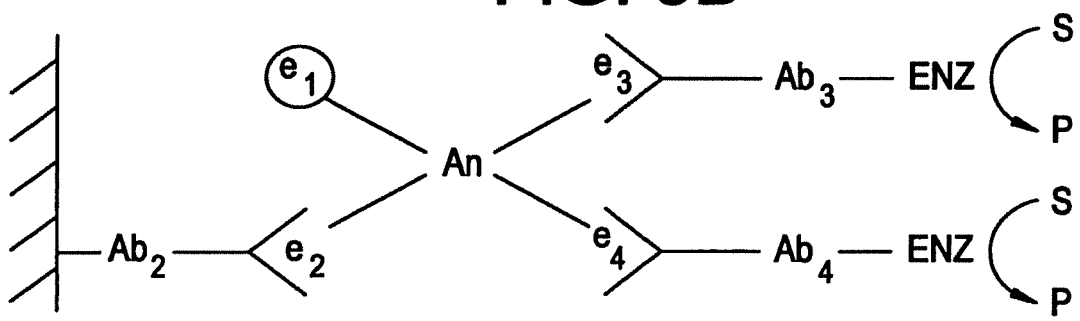
Figure 5C:
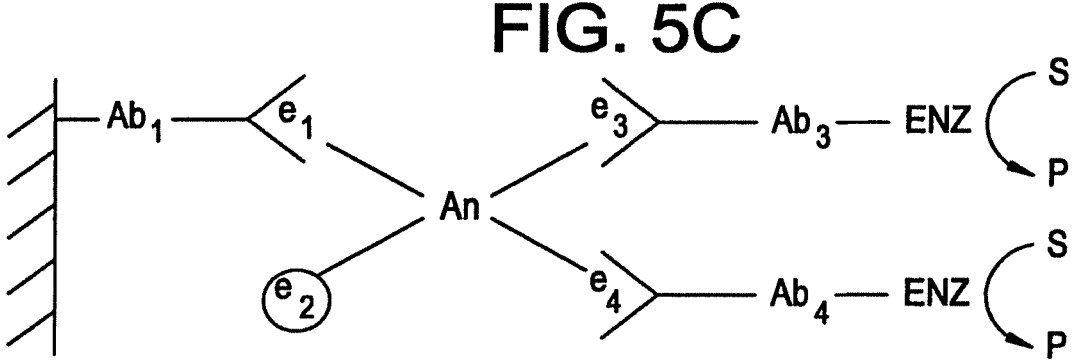
Figure 5D:
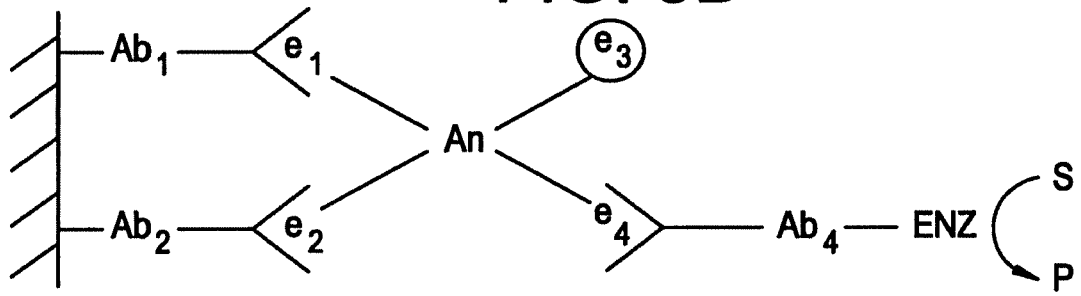
Figure 5E:
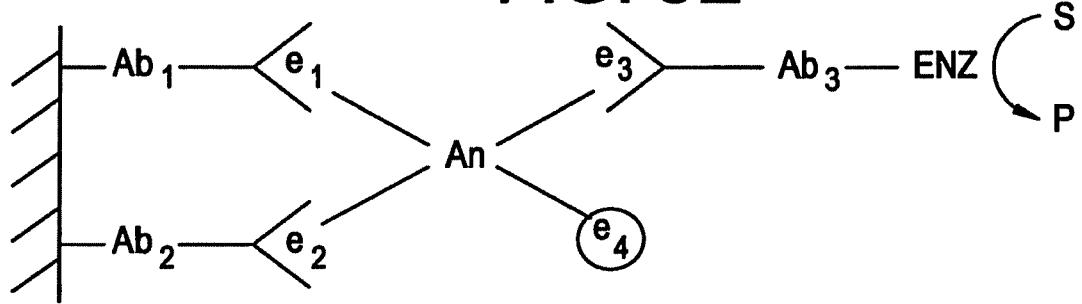
Figure 5F:
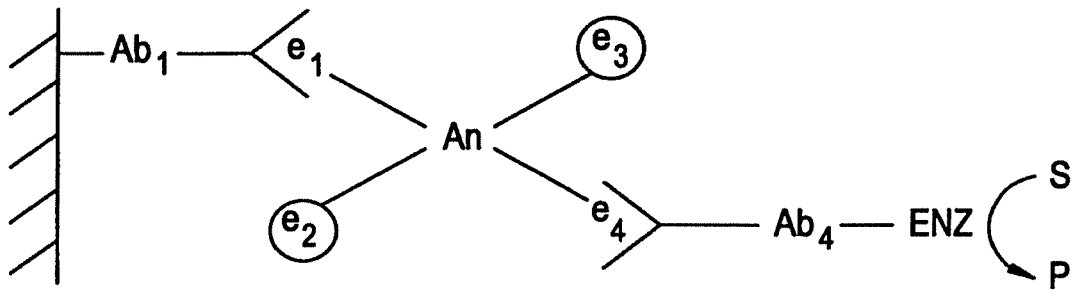
Figure 5G:
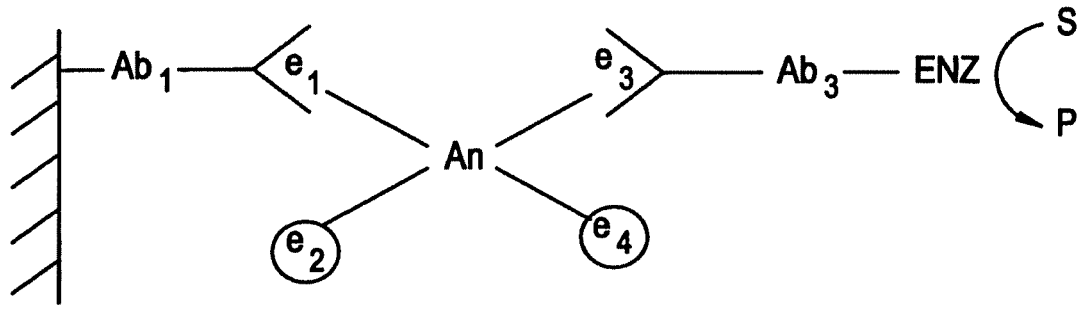
Figure 5H:
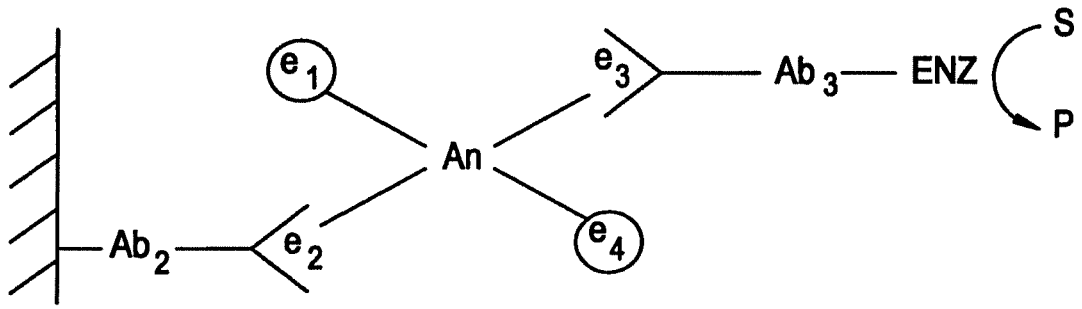
Figure 5I:
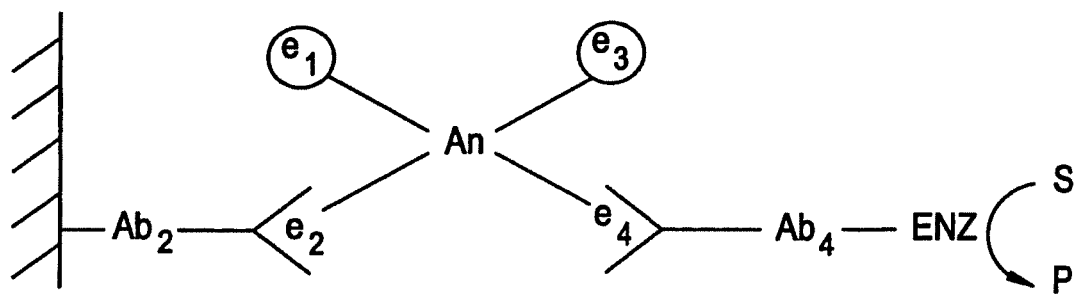

The analyte of interest and one or more subforms thereof may be detected by performing an immunoassay using antibodies specific for more than one epitope on the analyte either (i) on the capture side of the sandwich (FIG. 4), (ii) signal side of the sandwich (FIG. 3), (iii) or both (FIG. 5). By targeting at least three epitopes, in total, on the analyte of interest, the multiple sandwich assay of the present invention may detect the presence of the analyte and subforms thereof even if certain epitopes are unavailable for binding on the subform, so long as there is at least one epitope capable of binding by a capture antibody and at least one epitope available for binding by a signal antibody. The present invention is therefore able to detect analytes and multiple subforms thereof that appear within a sample.

One of skill in the art will recognize that the invention described herein may detect an analyte of interest by using any binding member that is capable of specifically binding to an epitope on the analyte of interest. Binding members include, but are not limited to, extracellular or intracellular receptors, polynucleotides, peptide nucleic acids, and derivatives thereof.

The use of multiple antibodies in the practice of the present invention is contrasted with the use of polyclonal antibodies in traditional sandwich assays; in addition, the present invention is superior. Within a given polyclonal preparation, the specific epitopes recognized and the ratio of various antibodies in the preparation is generally unknown. Furthermore, the epitopes recognized and the ratio of various antibodies vary between polyclonal preparations. Another deficiency in the polyclonal approach is that the binding of individual antibodies within the polyclonal preparation will have diverse binding affinities. As a result, a significant portion of polyclonal preparations are antibodies which have sub-standard analytical performances or which bind epitopes that compete with other antibodies in the preparation. By contrast, the present invention allows the preparation of controlled multi-epitopic reagents with more efficient assay characteristics because of better binding affinities and less reagent required for a given assay signal.

In one exemplary embodiment of the invention, the immunoassay is based on a first antibody attached to a surface (i.e., "capture antibody" or "capture reagent") and at least a second and third antibody, wherein each antibody binds to a different epitope on the analyte. The antibodies not attached to a surface may be labeled with a signal-generating element (i.e., "signal antibody" or "signal reagent"). See FIG. 3.

In another exemplary embodiment of the invention, the immunoassay is based on at least a first and second capture antibody and a third antibody. The antibody not attached to a surface may be a signal antibody. See FIG. 4.

In another exemplary embodiment of the invention, the immunoassay is based on at least a first and second capture antibody and at least a third and fourth antibody. The antibodies not attached to a surface may be signal antibodies. See FIG. 5.

4. Antibodies

The antibodies of the present invention may be any antibody that specifically binds to an epitope available for binding on an analyte of interest or a subform thereof. The antibodies of the present invention include antibodies of classes IgG, IgM, IgA, IgD, and IgE, and fragments and derivatives thereof including Fab, $F(ab')_2$ and single chain antibodies. The antibodies of the present invention include monoclonal antibodies, polyclonal antibodies, affinity purified antibodies, or mixtures thereof which exhibit sufficient binding specificity to an epitope of the analyte or subform thereof. Monoclonal antibodies and fragments and derivatives thereof are preferred in the practice of the invention. The antibodies of the present invention preferably bind to epitopes of the analyte sufficiently removed from each other such that the antibodies do not mutually interfere with binding to the analyte or subform thereof. Appropriate antibodies for an analyte of interest may be chosen by means of mapping combinations of available antibodies to known epitope sites on the analyte using methods known in the art.

Numerous methods exist for preparing antibody fragments, including the use of common enzymes such as pepsin, papain, ficin, and trypsin. For more information on antibody preparation and antibody fragmentation, see Harlow and Lane, Antibodies, A Laboratory Manual, Cold Spring Harbor Laboratory, N Y, 1988, which is hereby incorporated by reference.

The antibodies of the present invention may be specific for human cTnI. The antibodies may specifically recognize epitopes located on the primary sequence of cTnI as indicated in FIG. 9. The antibodies may also be chosen from those antibodies indicated in FIG. 9.

5. Capture

Figure 6A:
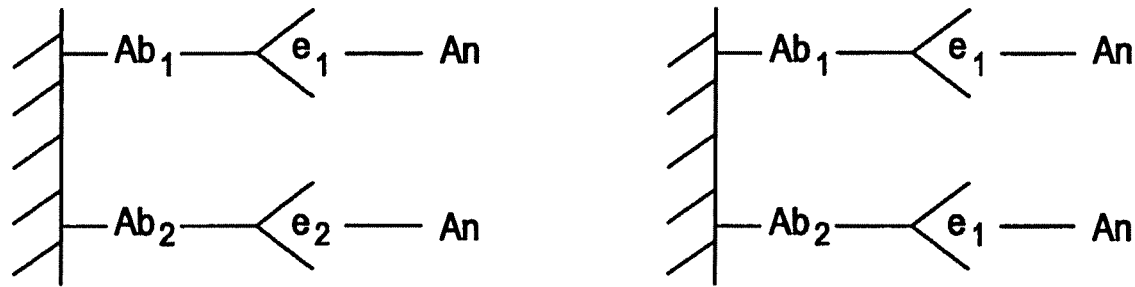
FIG. 6 shows one antibody ($Ab_1$) or more than one antibody ($Ab_1$ and $Ab_2$) binding to a different epilope ($e_1$ or $e_2$) on the analyte of interest (An) and conjugated to a common member, wherein the common member is a surface (FIG. 6A), microparticle (FIG. 6B), and a polypeptide, such as an enzyme (FIG. 6C).
Figure 6B:
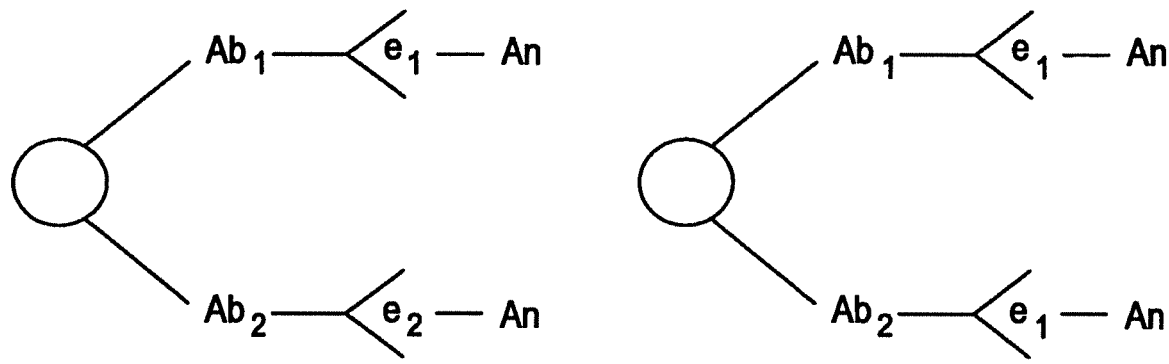

Capture antibodies of the present invention may be immobilized by conjugating one or more antibodies to a surface. See, e.g., FIG. 6A and FIG. 6B. A wide variety of compounds may be employed as the surface, the primary consideration being the binding of the antibody to the surface, the absence of interference with the signal generating element, and the absence of interference with the examination of the label. In particular, if a fluorescence or chromogenic spectrum is being measured, the surface should not provide interference.

Organic and inorganic polymers, both natural and synthetic, may be employed as the surface. Examples of suitable polymers include polyethylene, polypropylene, polybutylene, poly(4-methylbutylene), butyl rubber and other synthetic rubbers, silicone rubbers and silastic polymers, polyesters, polyimides, cellulose and cellulose derivatives (such as cellulose acetate, nitrocellulose and the like), acrylates, methacrylates, vinyl polymers (such as polyvinyl acetate, polyvinyl chloride, polyvinylidene chloride, polyvinyl fluoride, and the like), polystyrene and styrene graft copolymers, styrene-acrylonitrile copolymers, rayon, nylon, polyvinylbutyrate, polyformaldehyde, etc. Other materials which may be employed as the surface are silica gel, silicon wafers, glass, paper, insoluble protein, metals, metalloids, metal oxides, magnetic materials, semi-conductive materials, cements or the like. In addition are included substances that form gels, i.e., proteins such as gelatins, lipopolysaccharides, silicates, agarose, polyacrylamides or polymers which form several aqueous phases such as dextrans, polyalkylene glycols (alkylene with 2 to 3 carbon atoms) or surfactants, e.g. amphophilic compounds such as phospholipids, long chain (12-24 carbon atoms) alkyl ammonium salts and the like.

The surface may comprise polystyrene, styrene copolymers including styrene-(vinyl monomer) copolymers such as styrene-acrylonitrile copolymers, polyolefins such as polyethylene and polypropylene, and acrylate and methacrylate polymers and copolymers and mixtures thereof.

The surface may also comprise magnetizable materials in particulate form. Traditional interference by such magnetizable materials may be minimized by adding magnetizable particles to each of the reaction steps. Magnetic interference produced at each step may be made nearly equal, and thus is effectively cancelled. Magnetizable particles may be easily separated from the serum or other solution by application of a magnetic field to concentrate the particles.

The capture antibody may be bound to the surface by any method of bonding which does not significantly reduce the antibody binding sites and which binds sufficiently to permit separation of the surface from the liquids and rinse solutions without significant detachment of antibody from the surface. Non-covalent bonding may be achieved by adsorption, ionic bonding, van der Waals adsorption, electrostatic bonding, and other non-covalent bonding. The antibody may also be bound to the surface by covalent bonding.

Procedures for covalently adhering antibodies to surfaces are described by I. Chibata in IMMOBILIZED ENZYMES, Halsted Press, New York, 1978, and by A. Cuatrecasas, J. Bio. Chem. 245:3059 (1970), the entire contents of which are hereby incorporated by reference. The surface may be coated with a protein and coupled with antibody using the procedures described in U.S. Pat. No. 4,210,418 using glutaraldehyde as a coupling agent, for example. In an alternate procedure the surface may be coated with a layer having free isocyanate groups such as a polyether isocyanate. Application of the antibody in aqueous solution thereto effects the requisite bonding. In another procedure, the antibody may be coupled to a hydroxylated material by means of cyanogen bromide as described in U.S. Pat. No. 3,720,760. In a still further procedure, *Staphylococcus* Protein A may be bound to the surface, and the $F_c$ chain of the antibody can be conjugated with the Protein A.

Capture antibodies may be attached to a surface by adhesion followed by chemical crosslinking. Crosslinking agents which may be used include, but are not limited to, 1-ethyl-3-(3-dimethylaminopropyl)-carbodiimide (EDC), glutaraldehyde, adipic acid dihydrazide, bis-diazotized benzidine, 1,4-butane diglycidyl ether, bis-maleimido hexane, sulfosuccinimidyl 4-(N-maleimidomethyl)-cyclohexane-1-carboxylate, and N-hydroxysuccinimidyl 4-azidosalicylic acid. EDC may be used for any surface that has free carboxyl groups. These and many other similar reagents are well known in the art.

6. Conjugation of Antibodies to a Common Member

Figure 6C:
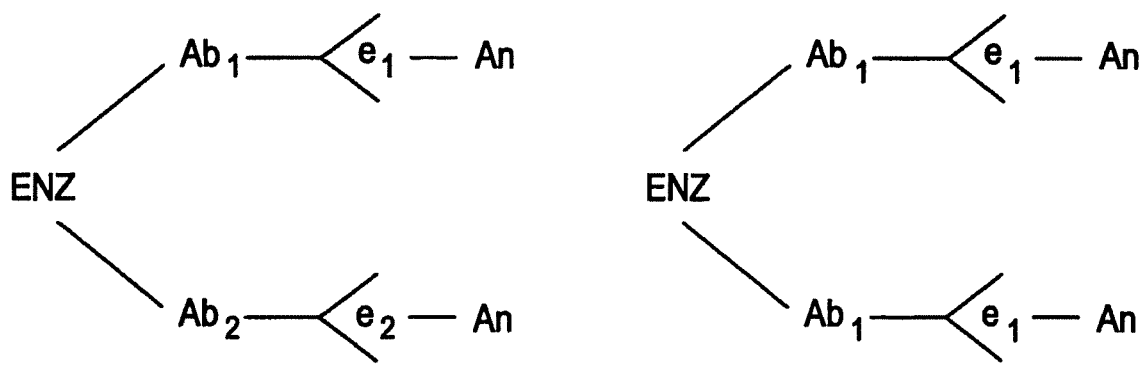

In another exemplary embodiment, the same or different antibodies may be conjugated to a common member, using any of the conjugation methods described above. Common members include, but are not limited to, a particle, microparticle (FIG. 6B), polypeptide (FIG. 6C), chemical linker, or a surface (FIG. 6A) as described above.

A common member may be conjugated with more than one antibody, each antibody binding to a different epitope on the analyte being assayed. See FIG. 6. The multiple antibodies may be conjugated to the common member at controlled molar ratios, for example using methods where the stoichiometry of the conjugation reaction is controlled.

Figure 7A:
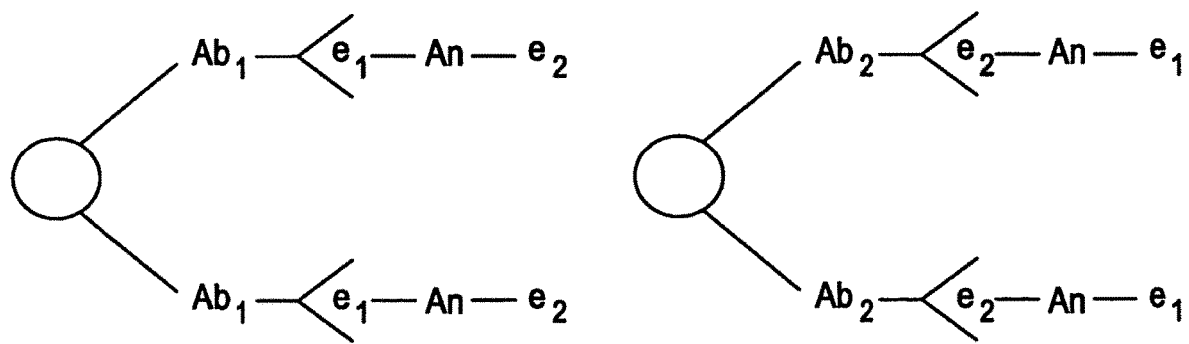
FIG. 7 shows a mixture of common members individually conjugated with a different antibody ($Ab_1$ or $Ab_2$), each antibody binding to a different epitope ($e_1$ or $e_2$) on the analyte being assayed (An), wherein the common member is a microparticle (FIG. 7A) or polypeptide, such as an enzyme (FIG. 7B).
Figure 7B:
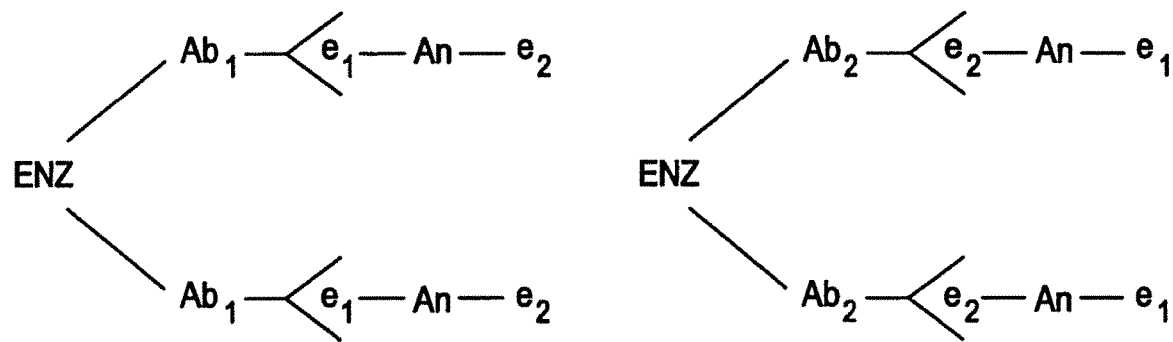
Figure 8A:
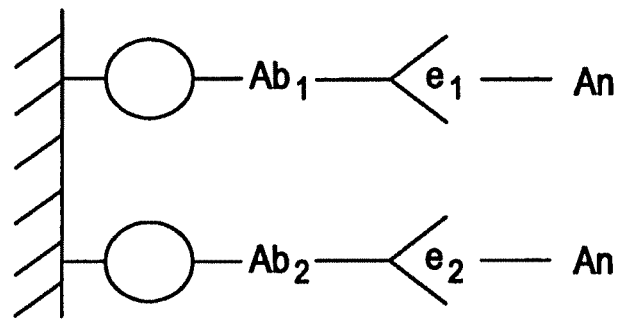
FIG. 8 shows a common member, such as a microparticle, conjugated to two or more antibodies ($Ab_1$ and $Ab_2$), conjugated to another common member, such as a surface, wherein two or more capture antibodies are either (i) individually conjugated to different microparticles (FIG. 8A), or (ii) conjugated together on a microparticle (FIG. 8B).
Figure 8B:
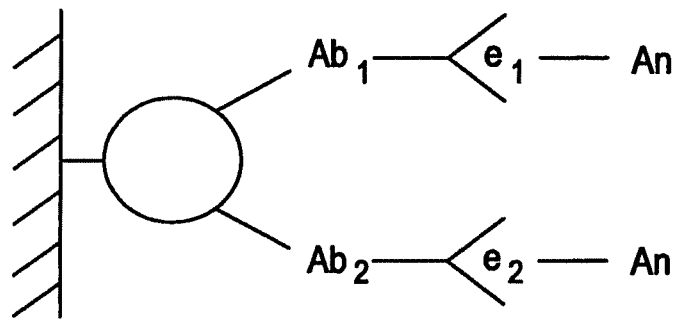

In addition, multiple common members may be individually conjugated with a different antibody, each antibody binding to a different epitope on the analyte being assayed. See FIG. 7. Molar ratios of the different antibodies may be controlled, using methods such as the mixing of multiple common members with conjugated antibodies.

a. Microparticle

Antibodies may be attached to microparticles using any of the conjugation methods described above. Various factors may be considered when choosing the coupling method including, but not limited to type and size of particle, coupling reagents, concentration of reactants, single or multi-step reaction, reaction buffer and pH, storage buffer, and blocking agents. For more information on using microparticles, see Bangs TechNote #201 "Working with Microspheres"; Bangs TechNote #204 "Adsorption to Microspheres"; Bangs TechNote #205 "Covalent Coupling"; Seradyn Technical Method Bulletin "Recommended Adsorption and Covalent Coupling Procedure" (1999); Hager, H. J. "Latex Polymer Reagents for Diagnostic Tests"; U.S. Pat. No. 3,857,931; and Wong, Chemistry of Protein Conjugation and Cross-Linking, 1991, CRC Press, Boca Raton, Fla., which are incorporated herein by reference.

7. Signal

Signal reagents may be prepared by conjugating an antibody to a signal-generating element by any of a number of common methods. Conjugates may be prepared, for example, by utilizing free sulfhydryl groups, generating sulfhydryl groups from available disulfide bonds, or introducing additional sulfhydryls onto the antibody. Linking agents, such as succinimydyi 4-(N-maleimidomethyl)cyclohexane-1-carboxylate (SMCC) may then be used to conjugate the activated antibody to the signal-generating element. For more information on preparing antibody conjugates, see Pierce Instructions "ImmunoPure 1gG1 Fab and F(ab')2 Preparation Kit" #44880; Pierce Instructions "SMCC, Sulfo-SMCC" #22360, #22322; Pierce Instructions "EZ-Link Maleimide Activated Phosphatase Kit"#31493; Beale, D. (1987) Molecular fragmentation: Some applications in immunology, Exp Comp Immunology 11, 287-296; Lamoyi, E. (1986) Preparation of F(ab')2 fragments from mouse IgG of various subclasses, Meth Enz 121, 652-663; King, T P, Kochoumian, L. (1979), A comparison of different enzyme-antibody conjugates for enzyme-linked immunosorbent assay, J Immun Meth 28, 201-210; Brinlday, Mass. (1992), A survey of methods for preparing protein conjugates with dyes, haptens and crosslinking reagents, Bioconj Chern 3, 2-13; and TechNote #204, "Adsorption to Microspheres", Bangs Laboratories Inc Rev. #001 Aug. 4, 1999, which are incorporated herein by reference.

Signal-generating elements of the present invention include, but are not limited to, radiolabels, metal particles, chromogens, fluorescent dyes, labeled proteins and enzymes. When the signal-generating element is an enzyme, the enzyme may catalyze a reaction wherein the depletion of substrate or the production of product can be detected. Exemplary enzymes include, but are not limited to, amylases, polynucleotidase, arginase, adenase, aminopolypeptidase, pepsin, lipases, catalase, tyrosinases, alcohol dehydrogenase, succinic dehydrogenase, diaphorase, glyoxalase, aldolase, glucose oxidase, horseradish peroxidase, beta-galactosidase, phosphatases, phosphorylases and hexokinases. Exemplary enzymes also include alkaline phosphatase, glucose oxidase, horseradish peroxidase, β-galactosidase and phenol oxidase. The enzymatic conversion of a substrate to a product may be measured by for example optical and electrochemical means.

a. Multiple Antibodies Conjugated to a Signal-Generating Element

The sensitivity of a sandwich assay is limited largely by the level of non-specific-adsorption of the signal reagent to the capture reagent and surfaces within the detection region of the analysis device. Such surfaces may include the walls of a cuvette, a wicking element, an electrode and the like. When the analyte is at low levels in a sample, a significant amount of the signal measured is background, and thus not related to the concentration of the analyte in the sample. The propensity of the signal reagent to non-specifically adsorb to surfaces within the analysis device may be a function of the inherent properties of the antibody and signal-generating element used to form the signal antibody, as well as the crosslinker. Additionally, the materials used in the analysis device (e.g., types of plastics) and the composition of the wash and substrate-containing solutions are generally optimized to minimize such non-specific protein adsorption. In particular, various surfactants, e.g. TWEEN® 20, BRIJ® 35, TRITON® X100, are almost invariably used in sandwich assays to minimize unwanted interactions of the signal reagents with other components within the assay device. Non-enzymatic proteins such as serum albumin, denatured proteins such as gelatins, and deactivated enzymes may also be added as surface blocking agents in order to lower the level of non-specific adsorption of the signal reagent. Even when all components of the assay are optimized, there is still usually a detectable level of non-specific signal reagent adsorption. The level of this non-specific adsorption is proportional to the amount of signal reagent used in the assay. Therefore, using less signal reagent or using the same molar amount of a lower molecular weight signal reagent will usually result in a lower background signal in the assay.

The signal reagent may comprise fragments of antibodies, such as Fab fragments, which may contribute to lowering the level of background signal. By lowering the molecular weight of the signal reagent, the time required for the binding step may be reduced due to diffusional considerations. The signal reagent may also comprise more than one antibody, which may also lower background signal levels by minimizing the overall size of the signal reagent while maximizing its ability to generate a signal in response to the presence of the analyte of interest. The more than one antibody of the signal reagent may bind to two or more different epitopes of the analyte, which may lead to stabilization of the signal antibody-analyte complex when more than one epitope of the analyte is bound by more than one antibody of the signal reagent.

When the signal reagent comprises more than one antibody, said antibodies may bind to one or more different epitopes.

A signal-generating element may be conjugated with more than one antibody, each antibody binding to a different epitope on the analyte of interest. See FIG. 6C. The molar ratio of antibodies conjugated to the signal-generating element may be controlled by selecting the reaction conditions and stoichiometry for the conjugation reaction.

A first antibody may be conjugated to a first signal-generating element and a second antibody may be conjugated to a second signal-generating element, each at a ratio greater than 1:1, and then mixed, wherein the first and second antibodies each bind to a different epitope on the analyte of interest. See FIG. 7B. The molar ratio of the first and second antibodies may also be controlled.

The signal-generating element may be conjugated to a single antibody, or two or more antibodies to different epitopes on the same analyte, wherein the signal antibody comprises a ratio of signal-generating element to a population of antibodies from about 1:100 to about 1:1.001. The signal-generating element may also be conjugated to a population of antibodies at a ratio from about 1:90 to about 1:1.001. The signal-generating element may also be conjugated to a population of antibodies at a ratio from about 1:80 to about 1:1.001. The signal-generating element may also be conjugated to a population of antibodies at a ratio from about 1:70 to about 1:1.001. The signal-generating element may also be conjugated to a population of antibodies at a ratio from about 1:60 to about 1:1.001. The signal-generating element may also be conjugated to a population of antibodies at a ratio from about 1:50 to about 1:1.001. The signal-generating element may also be conjugated to a population of antibodies at a ratio from about 1:40 to about 1:1.001. The signal-generating element may also be conjugated to a population of antibodies at a ratio from about 1:30 to about 1:1.001. The signal-generating element may also be conjugated to a population of antibodies at a ratio from about 1:20 to about 1:1.001. The signal-generating element may also be conjugated to a population of antibodies at a ratio from about 1:10 to about 1:1.001, about 1:20 to about 1:10, about 1:30 to about 1:20, about 1:40 to about 1:30, about 1:50 to about 1:40, about 1:60 to about 1:50, about 1:70 to about 1:60, about 1:80 to about 1:70, about 1:90 to about 1:80, and about 1:100 to about 1:90. The signal-generating element may also be conjugated to a population of antibodies at a ratio from about 1:5 to about 1:1.001, about 1:10 to about 1:5, about 1:15 to about 1:10, about 1:20 to about 1:15, about 1:25 to about 1:20, about 1:30 to about 1:25, about 1:35 to about 1:30, about 1:40 to about 1:35, about 1:45 to about 1:40, and about 1:50 to about 1:45. The signal-generating element may also be conjugated to a population of antibodies at a ratio of about 1:3.3.

The signal-generating element may be conjugated to a first and second antibody, each capable of binding to different epitopes on an analyte or subforms thereof, wherein the ratio of signal-generating element to total antibody is as disclosed above, and wherein the ratio of the first antibody to the second antibody is from about 1:50 to about 50:1. The ration of the first antibody to the second antibody may also be from about 1:10 to about 10:1, from about 1:5 to about 5:1, from about 1:3 to about 3:1, and from about 1:2 to about 2:1.

8. Signal and Detection

A signal may be produced by the signal-generating element, which may be measurable by a sensing element using methods which include, but are not limited to, radiation, optically, electrochemically, or by some other transduction means known in the art. A sensing element may be an electrode, biosensor, field-effect transistor, surface acoustic wave device, optical wave-guide, fiber optic, cuvette, radioactivity detector, reagents that facilitate, physical, nuclear, chemical, biochemical, electrical, or optical detection, or combinations thereof.

9. Immunoassay Device

The immunoassay of an analyte of interest may be conducted in an immunoassay device comprising one or more sensing elements and a surface on which a modified sandwich immunoassay is conducted as described above. The device surface may comprise two or more antibodies that are each capable of binding to different epitopes on the analyte. At least one of the two antibodies is also capable of binding to the same epitope on a subform of the analyte. At least one of the epitopes on the analyte is unavailable for binding on the subform.

Devices of the present invention include a cartridge, columns, syringe, cuvette, or other analytical device or system known in the art. The cartridge may be of a type as described in U.S. Pat. No. 5,096,669. Examples of other cartridge configurations are found in U.S. Pat. Nos. 5,416,026, 5,593,638, 5,447,440, 5,628,961, 5,514,253, 5,609,824, 5,605,664, 5,614,416, 5,789,253, 6,030,827, and 6,379,883. Still other cartridge configurations are described in PCT/US00/31158, PCT/US01/04345 and U.S. Pat. No. 7,419,821. The disclosures of the foregoing are hereby incorporated by reference.

The surface of the immunoassay device maybe of any appropriate surface known to those of skill in the art including, but not limited to, glass, semiconductor, plastic, silicon dioxide, photoformable PVA, photoformable gelatin, film forming latex, and conductive metal. A conductive metal surface may be silver, iridium, gold, platinum, and alloys thereof.

Antibodies may be absorbed, adsorbed or covalently attached to the surface of the immunoassay device. Antibodies may be absorbed into PVA, gelatin and latex layers or absorbed to their surfaces. Antibodies may be adsorbed to glass, metal, semiconductor, plastic, silicon dioxide, photoformable PVA, and conductive metal. The two or more antibodies may also be attached to a microparticle as discussed above, wherein the microparticle is attached to the surface as discussed above. The immunoassay device may also contain a third antibody which binds to a different epitope on the analyte.

The sensing element of the immunoassay device may be of any type known in the art including, but not limited to, an electrode, biosensor, field-effect transistor, surface acoustic wave device, optical wave-guide, fiber optic, cuvette, radioactivity detector, immunechromatographic device, reagents that facilitate, physical, nuclear, chemical, biochemical, electrical, optical detection, or combinations thereof.

10. Immunoassay Kit

An immunoassay kit may be used to detect an analyte of interest and subforms thereof in a modified sandwich immunoassay as described above. The kit may comprise three or more antibodies that are each capable of binding to different epitopes on the analyte. At least two of the three antibodies are also capable of binding to the same epitopes on a subform of the analyte. At least one of the epitopes on the analyte is unavailable for binding on the subform.

11. Sandwich Immunoassay Product

A sandwich immunoassay product may comprise an analyte of interest and a subform thereof. At least three epitopes on the analyte are available for binding by at least three different antibodies. The analyte may be bound by at least three different antibodies with each antibody binding to a different epitope on the analyte. At least two of the three epitopes on the analyte are available for binding on the subform by at least two of the at least three different antibodies. The subform may be bound by at least two of the three different antibodies that bind to the analyte with each antibody binding to a different epitope on the subform. At least one epitope of the analyte is unavailable for binding on the subform. At least one of the antibodies bound to the analyte and the subform of the analyte may be a signal antibody.

12. Method of Assaying for an Analyte

A sample may be immunoassayed for the presence of an analyte and subforms thereof by performing a modified sandwich immunoassay as described above. At least three different antibodies are used, wherein each antibody is capable of binding to a different epitope on the analyte. At least two of the antibodies capable of binding to the analyte are capture antibodies or signal antibodies, or a combination thereof. At least one of the epitopes on the analyte is unavailable for binding on the subform.

The sample to be immunoassayed is added to a surface comprising one or more capture antibodies. The one or more signal antibodies are then added. Alternatively, one or more signal antibodies may be added to the sample before or during application of the sample to the surface comprising one or more capture antibodies. After removing unbound signal antibodies, the extent of binding of the one or more signal antibodies is determined as described above. A signal will be produced by analyte as well as all subforms of the analyte that have at least one epitope that is present or capable of being bound by a capture antibody and at least a second epitope that is present or capable of being bound by a signal antibody.

13. Method of Diagnosing an Acute Disease

The analyte of interest and subforms thereof may be immunoassayed to determine whether a patient has suffered an acute medical event. A sample may be obtained from the patient and immunoassayed for the presence of the analyte of interest and subforms thereof by using the method of assaying described above. Signal produced by signal antibodies may be compared to control values. A signal, or a sequence of signals from a series of assays over a period of hours or days, detectable above control may indicate that the patient has suffered an acute medical event.

The acute medical event may be any disease state that is associated with a clinical marker, wherein the clinical marker is an analyte in the modified immunoassay described herein. The medical event may be for example a myocardial infarction. The analyte of interest may be for example TnI, TnT, TnC, CK-M, CK-B, CK-MB, myoglobin, TSH, FSH, CRP, BNP, pro-BNP, PSA, PCA, apolipoprotein, and combinations thereof.

14. Method of Diagnosing the Time of the Occurrence of an Acute Disease

The analyte of interest and subforms thereof may be immunoassayed to determine when a patient suffered an acute medical event. A sample, or set of samples obtained at different times, may be obtained from the patient and immunoassayed for the presence of the analyte of interest and subforms thereof by using the method of assaying described above. The amount of signal produced by signal antibodies may be correlated with a standard curve of amount of analyte vs. time to determine when the patient suffered the acute medical event. One of ordinary skill may produce the standard curve by using the methods described herein.

15. Method of Diagnosing the Severity of an Acute Disease

The analyte of interest and subforms thereof may be immunoassayed to determine the severity of an acute medical event suffered by a patient. A sample, or set of samples obtained at different times, may be obtained from the patient and immunoassayed for the presence of the analyte of interest and subforms thereof by using the method of assaying described above. The amount of signal produced by signal antibodies may correlate to the severity of a medical event suffered by the patient.

Having now generally described the invention, the following examples are provided in order to more fully illustrate the invention. These examples are for purposes of illustration only and are not intended to limit the scope of the invention.

Example 1

Conjugation of cTNI Capture Antibodies to a Particle

Bead particles conjugated with antibodies specific for cTnI were prepared by first exchanging polystyrene/acrylic acid latex 0.2 μm diameter spheres (Seradyn) into 0.05 M 2-(N-morpholino)ethanesulfonic acid (MES, Sigma Aldrich) buffer at pH 6.2. To a 2% w/w solution of the latex spheres was added cTnI antibodies (buffer exchanged into the same 0.05 M MES buffer) at a controlled mass ratio relative to the mass of the latex spheres. The solution was stirred for 15 minutes at 4° C. and the antibody coated beads separated via controlled centrifugation. Typically sufficient antibody was added to fully saturate the latex bead surface (8% to 15% of the mass of the latex particles). The microparticle centrifuged pellet was then resuspended into MES buffer at 1% w/v density and 1 to 10 mM of EDC was added to covalently crosslink the adsorbed antibody to the latex spheres. The suspension was allowed to react for 4 to 12 hours at which time the latex particles were separated by centrifugation, resuspended at 1% in the MES buffer and the EDC addition was repeated. Using the above method, microparticle capture reagents were made comprising either CB1 (19C7, Hytest Inc.) or CB2 (34503228P, Biospacific Inc.). CB12 microparticles comprising both CB1 and CB2 were prepared using the above method by adding a mixture of the two capture antibodies.

Example 2

Preparation of Signal Antibodies

The following method was used to prepare alkaline phosphatase (ALP) labeled Fab conjugates to be used as signal reagents. Alkaline phosphatase (Biozyme) was buffer exchanged into phosphate buffered saline (PBS). A 1 mg/ml to 15 mg/ml solution of the ALP was reacted with 25 weight percent (relative to the ALP weight in the solution) of the heterobifunctional crosslinker succinimidyl-4-[N-maleimidomethyl]-cyclohexane-1-carboxy[6-amidocaproate] (LC-SMCC, Pierce). The crosslinker was added as a solution in dimethyl sulphoxide (DMSO, Sigma). This solution was allowed to react at room temperature for 45 minutes, after which it was centrifuged to remove precipitates. The activated ALP was separated from unreacted LCSMCC via a Sephadex G50 desalting column (Sigma Aldrich).

Figure 12:
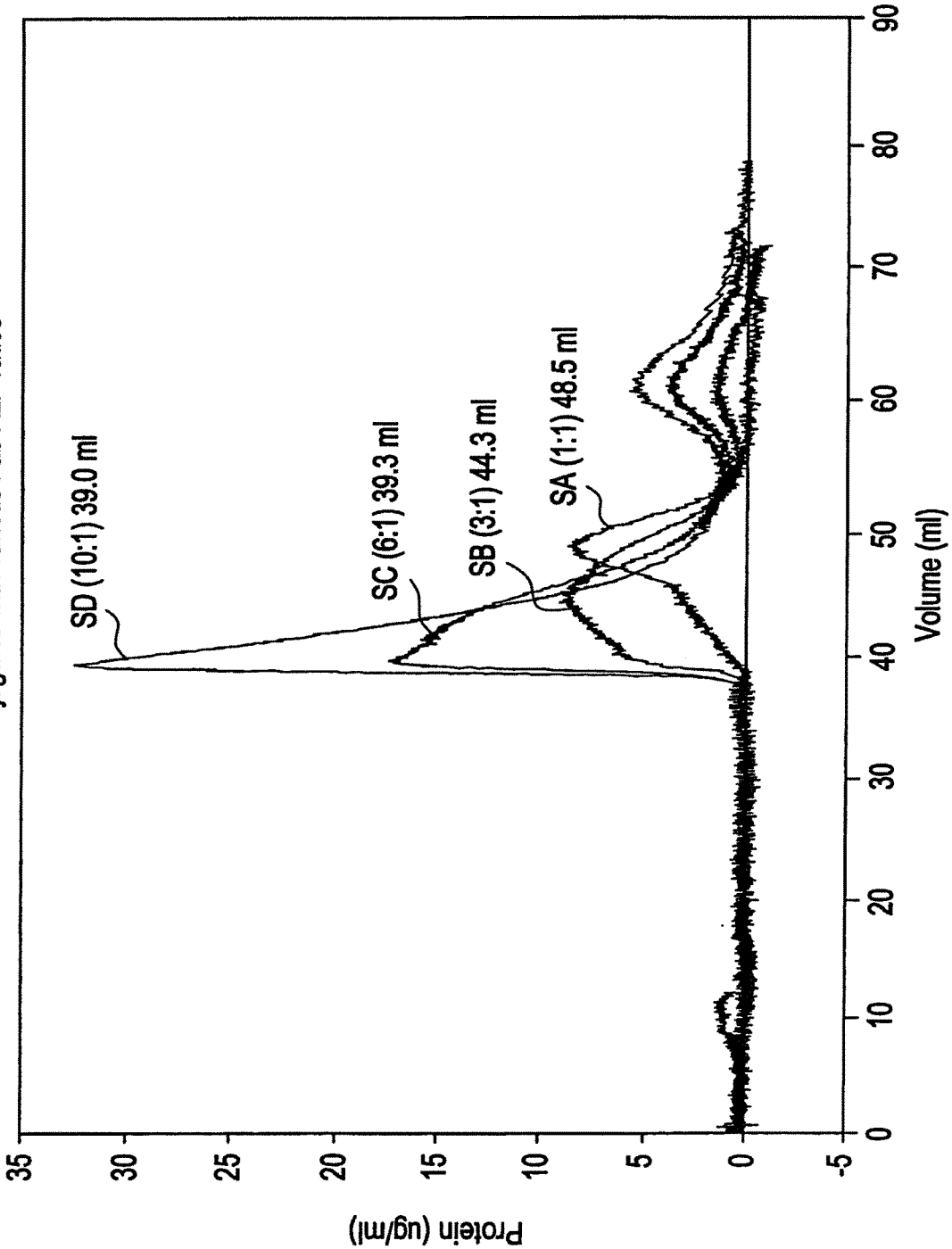
FIG. 12 shows elution profiles for Fab-ALP conjugates with different ratios of ALP to Fab.

Fab fragments of the antibodies to be incorporated into the signal reagent were formed via pepsin (Sigma) digestion of the whole antibodies and separated using a S200 sephacryl size exclusion column (Amersham Pharmacia). The resulting F(ab)$_2$ fragments were chemically reduced in 60 mM mercaptoethylamine (MEA, Sigma Aldrich) for 45 minutes at 37° C. to produce two Fab fragments, which were separated from excess MEA by desalting using a sephadex G50 column. The Fab fragments were then added to activated ALP and allowed to react at 4° C. for 2 to 12 hours. The reaction was quenched with an equal volume of 0.1 M glycine (Sigma), 0.01 M cysteine (Pierce) in PBS pH 7.4. The reaction products were then fractionated on a Sephacryl 5200 column to yield the signal reagent comprising Fab fragments. Signal reagents with specific molar ratios of Fab fragments to ALP were obtained by varying the ratio of Fab$_2$ fragments to ALP in the reaction above. FIG. 12 shows the elution profile for ALP-Fab signal reagents with ALP:Fab ratios of 1:1, 1:3, 1:6 and 1:10.

Using the above method, ALP-labeled signal reagents were made comprising either EC1 (G129C, Biospacific Inc.) or EC2 (G130C, Biospacific Inc.). EC12 signal reagents comprising both EC1 and EC2 were prepared using the above method by mixing the two fab fragments at a molar ratio of 1:1 before adding the mixture to activated ALP.

Example 3

Preparation of an ELISA Sensor with cTnI Capture Antibodies

The following method was used to prepare an analyte detector comprising an immobilized layer of antibody labeled particles on an ELISA sensor. Briefly, amperometric sensors used in the analyte detector are fabricated using traditional semiconductor thin layer techniques on oxidized silicon wafers. The cTnI capture regions are produced by microdispensing solutions of the capture antibodies described in Example 1 using methods described in U.S. Pat. No. 5,554,339. Droplets of the particle-containing suspension are allowed to dry to form cTnI capture regions on the sensor surface. The sensor chips are assembled with a separated electrochemical grounding chip into a plastic base covered with a two sided adhesive tape gasket, laser cut with openings for the sensors, ground chip and fluidic channels. To this base assembly a plastic cover is added to form fluidic conduits. The enzyme labeled signal reagent of Example 2 is printed onto the same ELISA sensor as the capture antibodies. The signal reagent is formulated in a 1% to 50% sugar solution containing PBS and a preservative. This composition was found to provide rapid dissolution of the signal reagent into a blood sample. The assembled cartridge is pressed to yield the disposable cartridge, which may be used in a portable electrochemical analyzer.

Example 4

Comparison of Detection of cTnI Using Single or Multiple Capture Antibodies

An analytical system for measuring cTnI was used of the general type described in U.S. Pat. No. 5,096,669, which is hereby incorporated by reference. Briefly, cartridges for assaying cTnI were produced using sensors coated with latex microsphere comprising CB1, CB2 and CB12 capture reagents, as described in Example 3. cTnI was assayed in three whole-blood samples to which either free cTnI (Scripps Laboratories) or ITC complex (Hytest Ltd) was added. The signal reagent EC12, as described in Example 2, was used to produce an amperometric signal based on dephosporylation of a substrate by ALP to produce an electroactive product. The amount of electroactive product is proportional to the amount of detectable cTnI.

FIG. 10 shows high signal levels for cartridges comprising the CB1 capture reagent for both free cTnI (diamond points) and the two levels of ITC complex (square and triangle points). By contrast, cartridges comprising the CB2 capture reagent yield lower signals, especially for the ITC complex. Cartridges using the CB12 hybrid capture reagent show improved signal generation for both forms of cTnI relative to either CB1 or CB2 capture reagents. The improved performance of the CB12 capture reagent is surprising, because the hybrid reagent comprises the CB2 antibody that by itself has markedly lower analytical performance than the CB1 antibody.

Example 5

Figure 11:
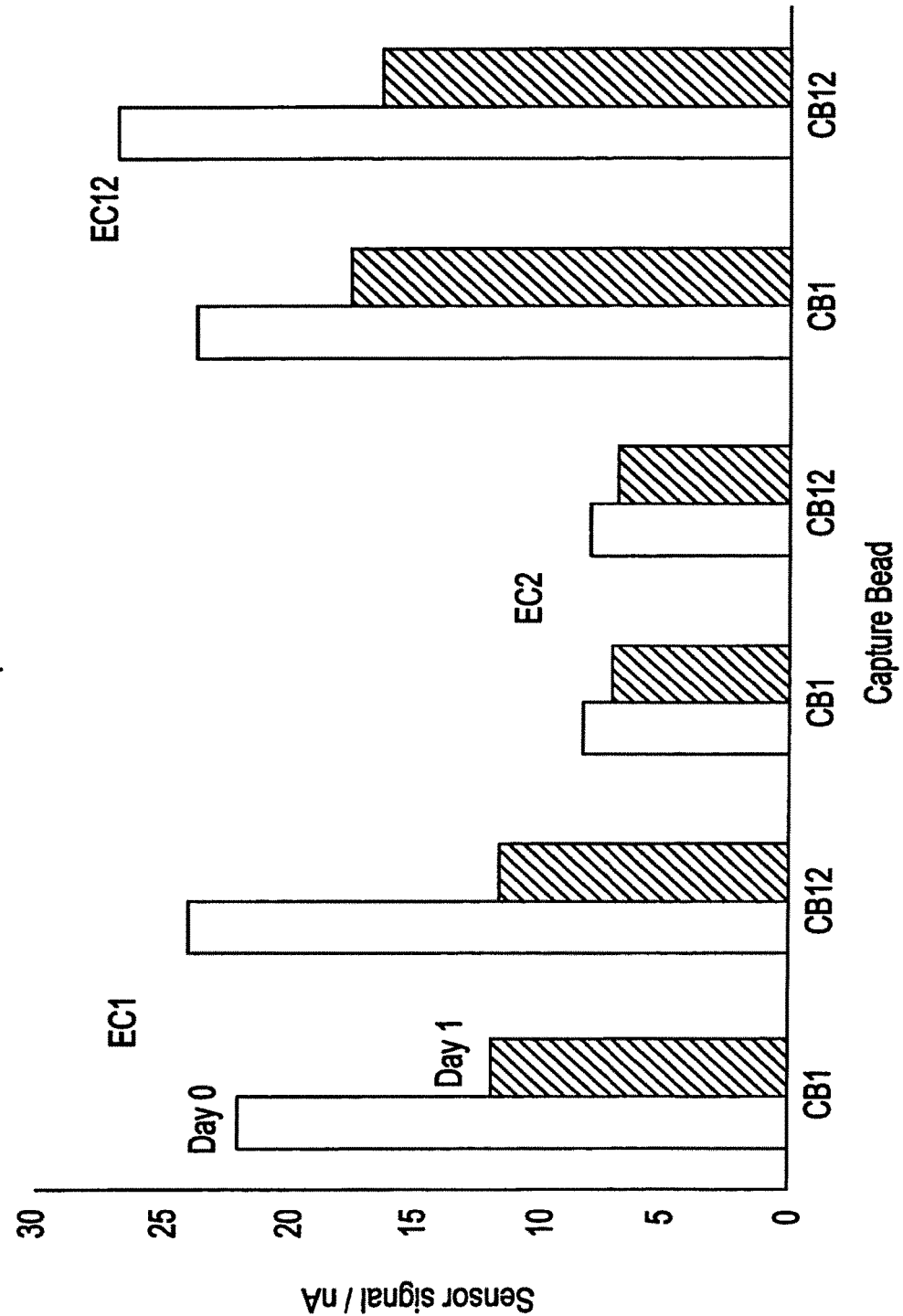
FIG. 11 shows a plot of the average signal obtained from a whole blood sample spiked with 6.0 ng/mL cITC complex immediately after preparation and after one-day incubation at room temperature using cartridges prepared with either CBI or CB12 coated sensors and with a signal producing enzyme conjugated to a first antibody (EC1), a second antibody (EC2) or a mixture of EC1 and EC2 (ECI2).

Comparison of Detection of cTnI Using Single or Multiple Signal Antibodies cTnI was assayed in a whole blood sample spiked with a 6.0 ng/mL cITC complex immediately after preparation and after a one-day incubation at room temperature using cartridges with sensors coated with latex microsphere comprising CB1 and CB12 capture reagents, as described in Example 3, and EC1, EC2 or EC12 signal reagents as described in Example 2. FIG. 11 demonstrates that the EC1 signal reagent shows a higher signal generation than the EC2 signal reagent. After a one day incubation of the sample to simulate aging of cTnI (e.g., proteolytic degradation), the signal level for the EC1 signal reagent drops significantly. In contrast, the EC2 signal reagent shows only a modest drop in the signal level. The signal generation of the hybrid signal reagent EC12 is surprisingly superior to each of the two single antibody signal reagents, especially after incubating the sample for one day.

Example 6

Detection of cTnI in Serum as a Diagnosis of Myocardial Infarction

Whole blood samples are obtained from patients suspected of suffering a myocardial infarction, as well as from control individuals. cTnI is assayed in the whole blood samples using cartridges with sensors coated with latex microsphere comprising CB12 capture reagents, as described in Example 3, and EC12 signal reagents as described in Example 2. The signal generated in samples derived from patients suspected of suffering an MI is compared to the level of signal from controls. Levels of signal greater than control indicate that the patient has suffered a MI.

We claim:

1. A cartridge for sensing at least one analyte in a sample, said cartridge comprising:
    a housing;
    at least one sensor located within the housing;
    a cavity within the housing including a sealed deformable pouch for retaining an aqueous reagent out of contact with the sensor;
    an aqueous reagent conduit for connecting the cavity to the sensor;
    aqueous reagent displacer under control of a reading apparatus for displacing the aqueous reagent from the cavity through the aqueous reagent conduit to the sensor;
    sample holding chamber within the housing, for retaining the sample out of contact with the sensor, prior to sensing;
    sample collector within the housing including an orifice for drawing the sample into the sample holding chamber;
    a sample conduit connecting the sample holding chamber with the sensor;
    sample displacer for forcibly displacing the sample from said sample holding chamber through the sample conduit and into contact with the sensor to permit sensing; and
    an immunoassay composition for detecting said analyte comprising at least three different antibodies, the at least three different antibodies being capable of binding to at least three different epitopes on said analyte, in which at least two of the at least three different antibodies are capable of binding to at least two different epitopes on a subform of said analyte, and in which at least one of the at least three different epitopes on said analyte is unavailable for binding on the subform.

2. The cartridge of claim 1, wherein said analyte is human cTnI and wherein the sample is a whole blood sample.

3. The cartridge of claim 1, wherein said at least three different antibodies comprise:
    (a) G129C antibody;
    (b) G130C antibody; and
    (c) at least one additional troponin I antibody different from (a) and (b).

4. The cartridge of claim 2, wherein (c) is selected from the group consisting of 19C7, A34720, 8E10, A34500, A34440, A34730, and 34503228P.

* * * * *